(12) United States Patent
Lapanashvili et al.

(10) Patent No.: US 6,832,982 B1
(45) Date of Patent: Dec. 21, 2004

(54) METHOD OF TREATING A LIVING ORGANISM TO ACHIEVE A HEART LOAD REDUCTION, AND APPARATUS FOR CARRYING OUT THE METHOD

(75) Inventors: Larry V. Lapanashvili, Winterthur (CH); Christian Sturzinger, Winthertur (CH)

(73) Assignee: Coral Licensing International Ltd., Tortola (VG)

( * ) Notice: Subject to any disclaimer, the term of this patent is extended or adjusted under 35 U.S.C. 154(b) by 39 days.

(21) Appl. No.: 10/069,333

(22) PCT Filed: Aug. 14, 2000

(86) PCT No.: PCT/EP00/07933

§ 371 (c)(1),
(2), (4) Date: Jul. 15, 2002

(87) PCT Pub. No.: WO01/13990

PCT Pub. Date: Mar. 1, 2001

Related U.S. Application Data

(63) Continuation-in-part of application No. 09/378,181, filed on Aug. 20, 1999, now Pat. No. 6,450,942.

(51) Int. Cl.[7] .............................................. A61N 1/365
(52) U.S. Cl. ........................................................ 600/16
(58) Field of Search ....................... 600/16, 17; 607/17, 607/23, 25, 72–74, 88; 128/907; 601/150–153

(56) References Cited

U.S. PATENT DOCUMENTS

| | | |
|---|---|---|
| 3,859,989 A | 1/1975 | Spielberg |
| 3,911,898 A | 10/1975 | Leachman |
| 4,077,402 A | 3/1978 | Benjamin |
| 4,269,175 A | 5/1981 | Dillon |
| 4,343,302 A | 8/1982 | Dillon |
| 4,541,417 A | 9/1985 | Krikorian |
| 4,590,925 A | 5/1986 | Dillon |
| 4,809,676 A | 3/1989 | Freeman |
| 5,084,281 A | 1/1992 | Dillon |
| 5,279,283 A | 1/1994 | Dillon |
| 5,313,942 A * | 5/1994 | Platzker ...................... 600/384 |
| 5,370,603 A | 12/1994 | Newman |
| 5,377,671 A | 1/1995 | Biondi |
| 5,458,626 A | 10/1995 | Krause |
| 5,514,079 A | 5/1996 | Dillon |
| 5,554,103 A | 9/1996 | Zheng |
| 5,707,400 A | 1/1998 | Terry |
| 5,820,567 A | 10/1998 | Mackie |

FOREIGN PATENT DOCUMENTS

| | | |
|---|---|---|
| DE | 7040406 | 4/1971 |
| DE | 2935204 | 3/1980 |
| DE | 3228977 A1 | 2/1983 |

(List continued on next page.)

OTHER PUBLICATIONS

English translation of Abstract of EP 0847776A1.
Microstim brochure relating to Microstim P2HD.
INFONET (Infodoc )1509, p. 2, SU 1648470 A, Abstract.

(List continued on next page.)

*Primary Examiner*—Jeffrey R. Jastrzab
(74) *Attorney, Agent, or Firm*—Townsend and Townsend and Crew LLP

(57) ABSTRACT

An apparatus and method for treating a mammal or other living organism having a heart and a peripheral vascular system to achieve a heart load reduction, said organism having a pulse rate and a systolic pressure resulting from the action of the heart, the method and apparatus involving the steps of measuring the heart rhythm, producing pressure pulsations in the peripheral vascular system by a non-invasive or invasive method in synchronization with the heart rhythm in the counterpulsation mode and varying at least one parameter of an input system generating said pressure pulsations to produce an optimised reduction in at least one of said pulse rate and said systolic pressure and hereby a net reduction in said heart load, said heart load being a function of said pulse rate and said systolic pressure.

40 Claims, 18 Drawing Sheets

Figure 2A:
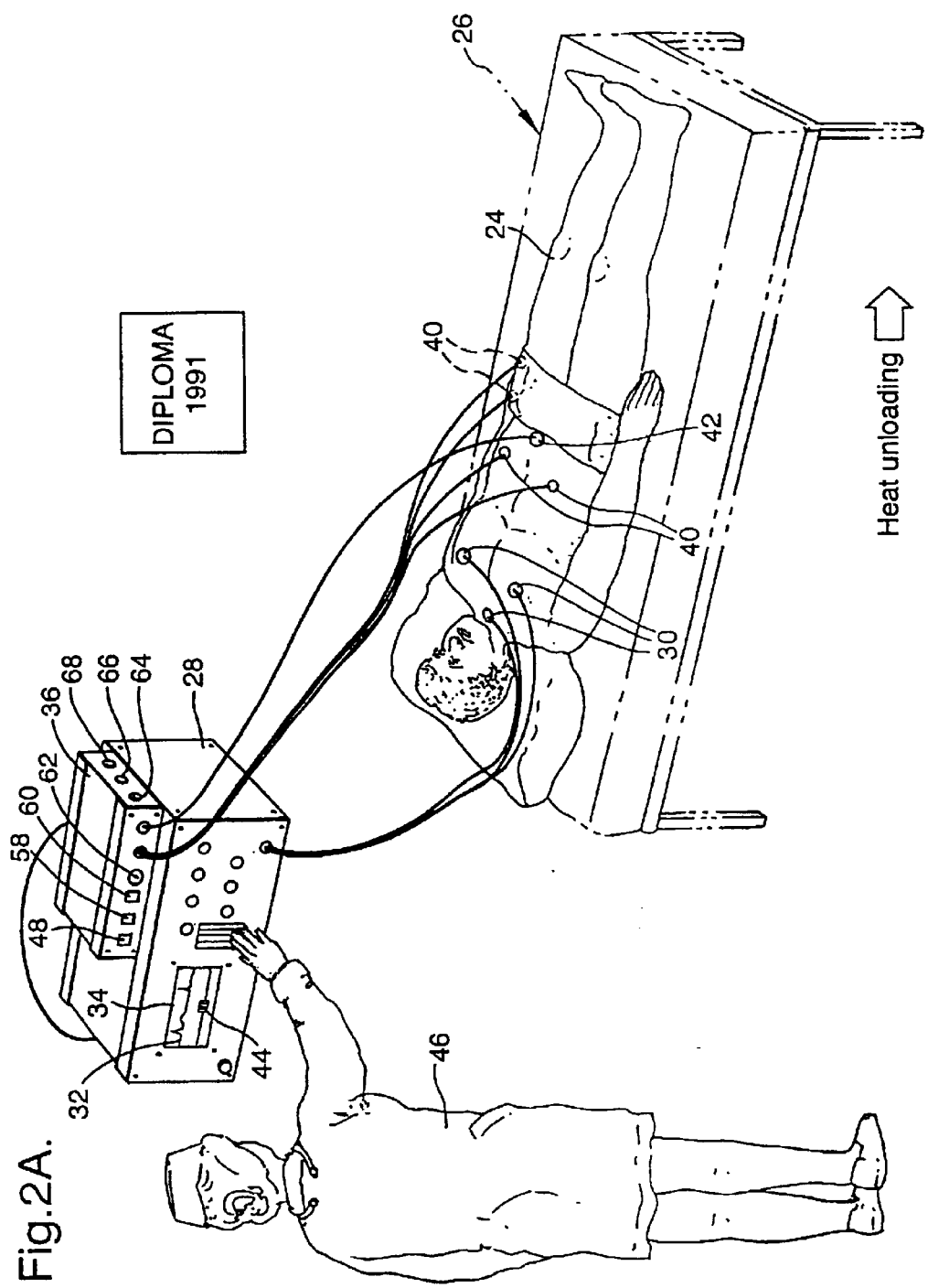

ECG=Electrocardiogram
MP=Muscular power
AoP=Aorta pressure
LVP=Left ventricular pressure Cardiac Rythm A=Normal situation
Cardiac Rythm B=Beginning of stimulation
Cardiac Rythm C=During stimulation

FOREIGN PATENT DOCUMENTS

| | | | |
|---|---|---|---|
| DE | 0109627 | A1 | 5/1984 |
| DE | 3533597 | A1 | 4/1987 |
| DE | 2944574 | C2 | 10/1987 |
| DE | 3804016 | A1 | 8/1989 |
| DE | 4137154 | A1 | 5/1993 |
| DE | 4338758 | A1 | 5/1994 |
| DE | 4311375 | A1 | 10/1994 |
| DE | 4314269 | A1 | 11/1994 |
| DE | 19543211 | A1 | 5/1997 |
| DE | 19651600 | A1 | 6/1998 |
| DE | 19716166 | A1 | 10/1998 |
| DE | 19813836 | A1 | 10/1999 |
| EP | 0203310 | A2 | 12/1986 |
| EP | 0268366 | A2 | 5/1988 |
| EP | 0329765 | B1 | 3/1993 |
| EP | 0547733 | A2 | 6/1993 |
| EP | 0569308 | A1 | 11/1993 |
| EP | 0573946 | A2 | 12/1993 |
| EP | 0504225 | B1 | 2/1994 |
| EP | 0587269 | A2 | 3/1994 |
| EP | 0504323 | B1 | 2/1995 |
| EP | 0416467 | B1 | 7/1995 |
| EP | 0605544 | B1 | 1/1996 |
| EP | 0620746 | B1 | 4/1996 |
| EP | 0712604 | A2 | 5/1996 |
| EP | 0721786 | A2 | 7/1996 |
| EP | 0482350 | B1 | 12/1996 |
| EP | 0673223 | B1 | 2/1997 |
| EP | 0759309 | A2 | 2/1997 |
| EP | 0798016 | A2 | 10/1997 |
| EP | 0847776 | A1 | 6/1998 |
| EP | 0722348 | B1 | 10/1998 |
| GB | 1359005 | | 7/1974 |
| GE | 366 | | 7/1996 |
| WO | WO 97/11737 | | 4/1997 |
| WO | WO 98/05379 | | 2/1998 |
| WO | WO 99/04833 | | 2/1999 |
| WO | WO 99/36028 | | 7/1999 |

OTHER PUBLICATIONS

INFONET (Infodoc )1509, p. 2, SU 1509045 A, Abstract.

Patent Abstracts of Japan, JP 09313621 A, Dec. 9, 1997, Abstract.

Cheever, Erik A., et al., "A Versatile Microprocessor–Based Multichannel Stimulator for Skeletal Muscle Cardiac Assist", *IEEE Transactions on Biomedical Engineering*, 45(1), Jan. 1998, pp. 56–67.

Theres, H., et al., "Frequenzadaptive Schrittmacherstimulation", *Münch. med. Wschr.* 129(1987), No. 46, pp. 847–850.

Lapanashvily, L.V., "Automuscolar System of Assisted Circulation for Surgical Correction of Cardiac Failure" in: *IL Cuore* vol. 9 No. 1 Jan./Feb. (1992), pp. 5–27.

User's Manual for The P4–Physio Model (Microstim neuromuscular stimulator) by VALMED S.A., 11/96 issue.

Circular Boot Corp., copy of "What is a Circular Boot?", Web pages downloaded on Jun. 29, 1999 (23 pages).

\* cited by examiner

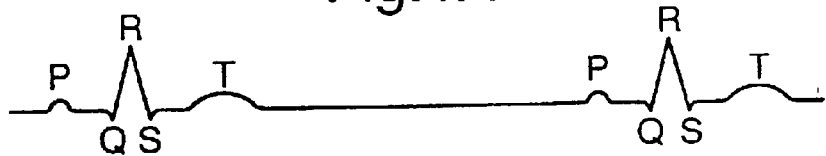
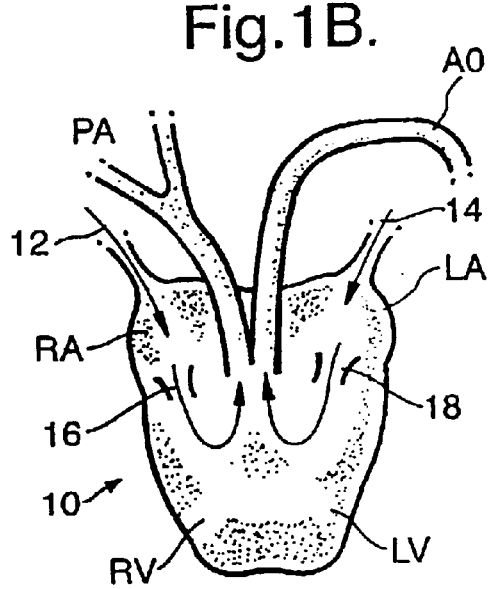
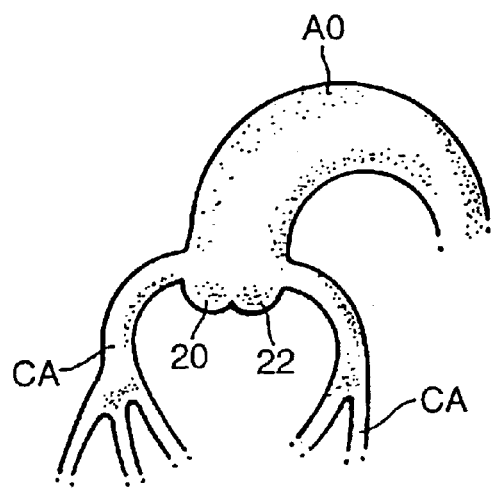

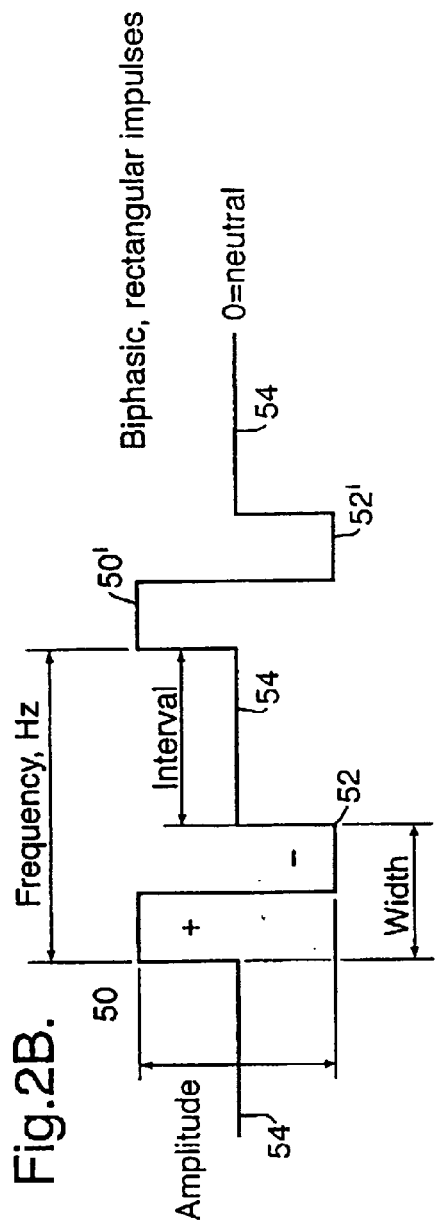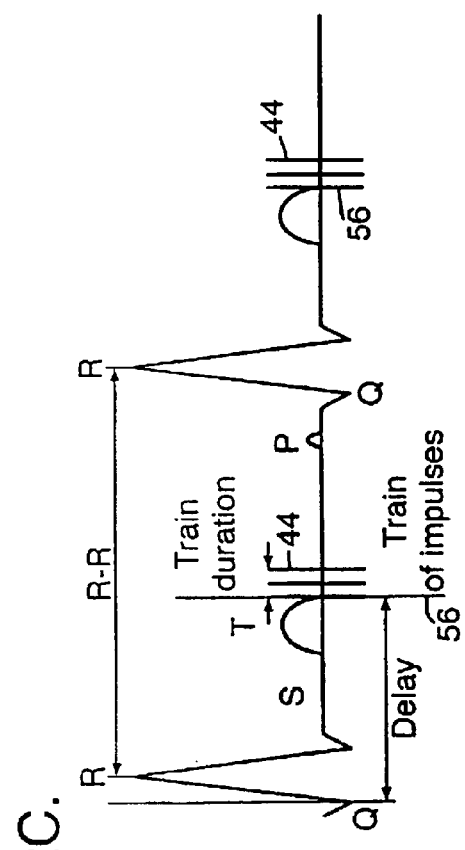

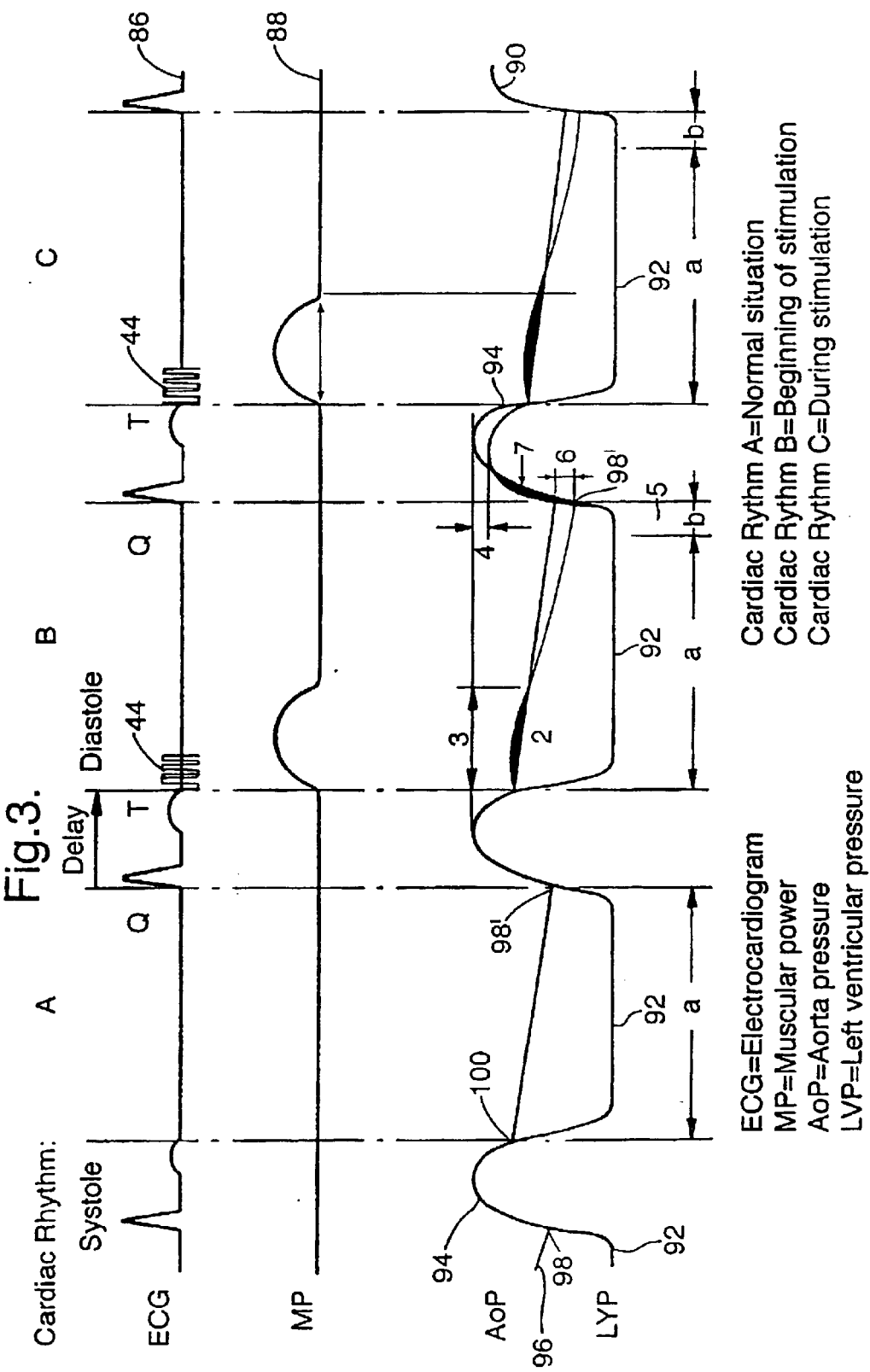

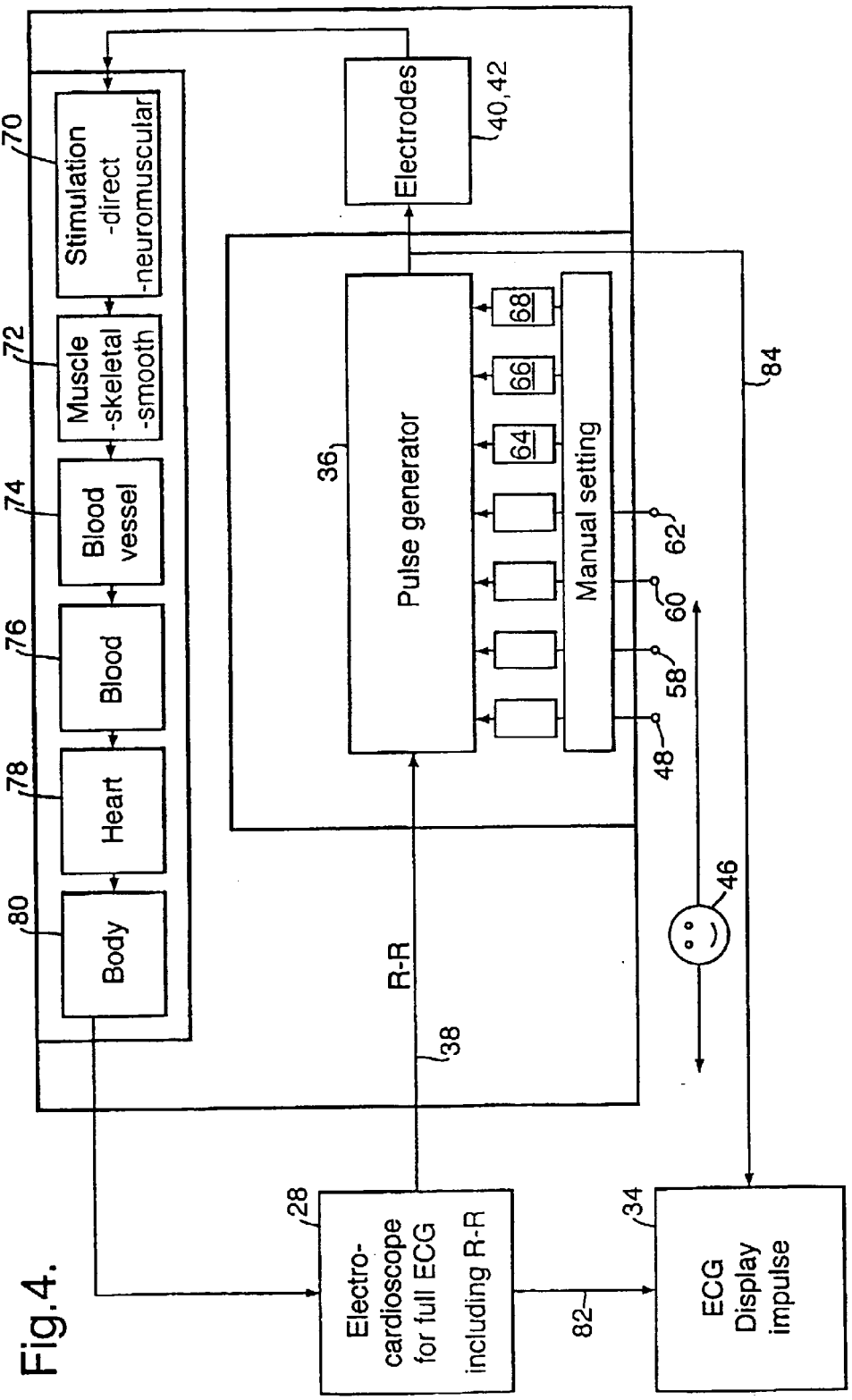

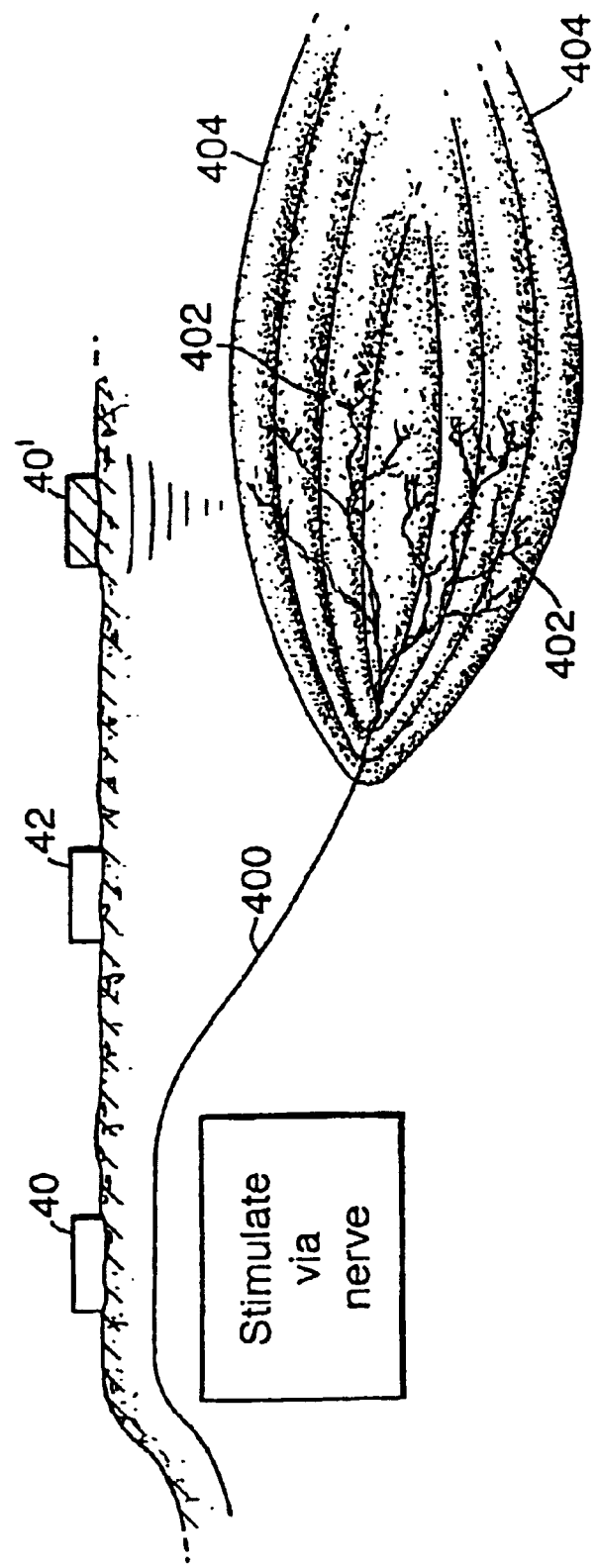

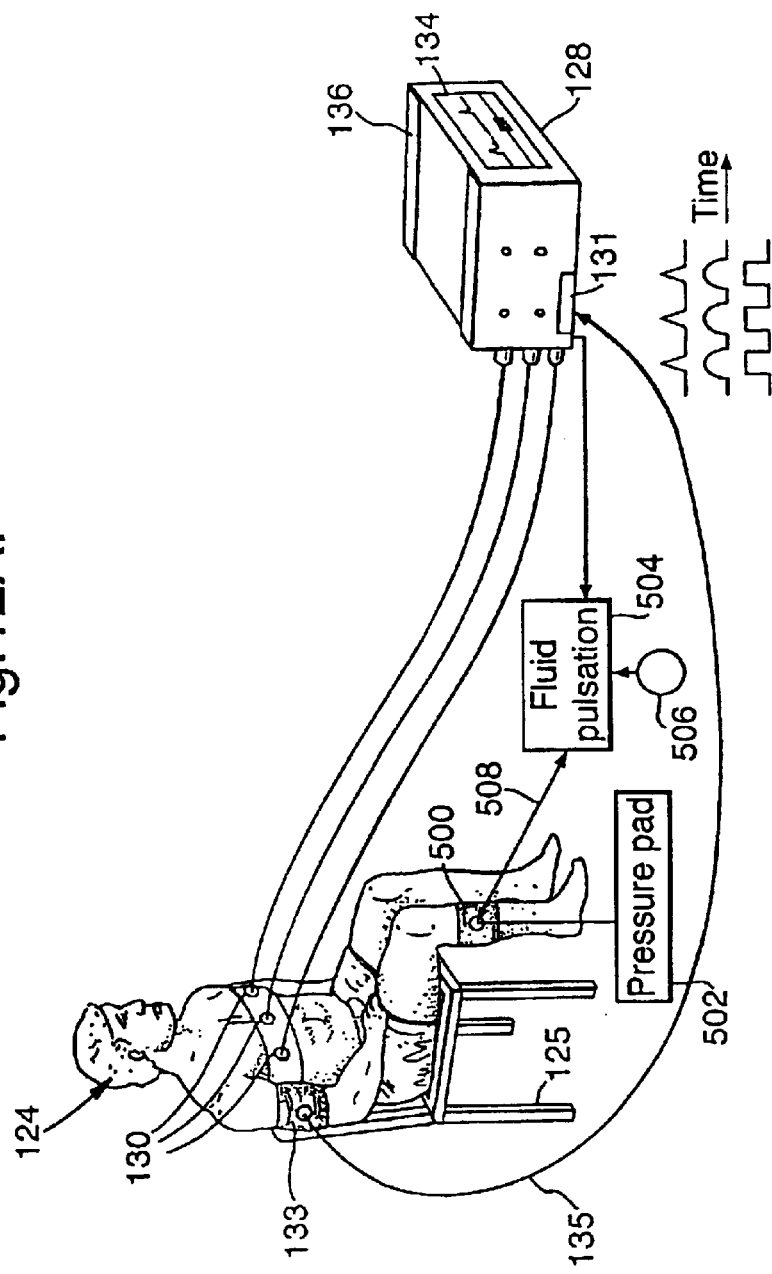

METHOD OF TREATING A LIVING ORGANISM TO ACHIEVE A HEART LOAD REDUCTION, AND APPARATUS FOR CARRYING OUT THE METHOD

The present invention relates to a method of treating a mammal or other living organism having a heart and a peripheral vascular system, in particular a human being to achieve a heart load reduction and a whole variety of other treatments and associated benefits as well as to an apparatus for carrying out the method.

To assist an understanding of the invention it is first necessary to consider the working of the human heart and the known prior art in this field.

The condition of the human heart is frequently measured by means of an electrocardiogram, the typical output trace that is obtained can, for example, be seen from FIG. 1. An electrocardiogram is basically a record of the sequence of electrical waves generated at each heart beat and the different peaks of the typical electrocardiogram are usually designated by the letters P, Q, R, S and T. The so-called R-R path, i.e. the time between two R peaks represents one cycle of the heart and normally amounts to about 1 second.

Of particular interest is not only the R-R path which corresponds to the frequency of the heart or the pulse rate, but rather also the Q-T path which reproduces the working performance of the heart, called the systole. The remainder of the path equivalent to R-R minus Q-T. i.e. T-Q effectively represents the recovery time of the heart in each heart beat, called the diastole. The operation of the human heart is discussed later in more detail with reference to FIGS. 1A, 1B and 1C.

Cardiologists frequently refer to the concept of the heart load which is proportional to the heart pulse rate, i.e. the frequency of R-R waves measured in heart beats per minute, multiplied by the systolic blood pressure as measured in millimeters of mercury.

Many treatments have been proposed and used in the prior art which affect the cardiovascular system of human beings. Well known amongst such systems are electrophysiological methods and apparatus which, for example, use electrical stimulation to produce muscle contractions which result in working and training of the muscles. The contractions and elongations caused by electrical stimulation improve the blood flow through the muscles and improve the muscle quality without effort on the part of the patient being treated.

Electrophysiological interactions with living bodies in general, and human beings in particular, can be classified into two main groups, namely asynchronous and cardiosynchronized electrophysiological interactions.

Asynchronous electrophysiological methods and apparatus operate using electrostimulation in which the stimulation is timed in accordance with some externally imposed rhythm, but this timing is not synchronized with the heart pulse rate. Known examples of asynchronous electrophysiological methods and apparatus include:

neurostimulation and neuromuscular and direct muscular stimulation by electrostimulators, with equipment being available from Medicompex SA, Valmed SA, Nemectron GmbH, and EMPI Inc. among others, the use of electrostimulation for the therapy of pain, with equipment being available from Medtronic Inc. among others, electrostimulation for active tremor control therapy, for which Medtronic Inc. among others supplies equipment and electrostimulation for urinary control, again with apparatus being offered by, for example, Medtronic Inc., such as that company's Interstim product.

All the above asynchronous stimulation methods certainly bring benefits to the areas being treated, but result in an increase of the heart load when compared to a normal situation, i.e. without electrostimulation. This heart loading is even known to include an inherent risk of producing arrhythmia or heart problems, when the electrostimulation is applied near the heart on the chest muscle and especially on the left hemithorax.

A useful summary of electrical stimulation therapy is to be found on pages 3 and 4 of the "Users Manual" produced by Valmed SA in relation to their Microstim (registered trade mark), neuromuscular stimulator P4 Physio Model, issue 11/96.

The other basic category of electrophysiological techniques, namely cardiosynchronized electrophysiological methods and apparatus, comprise methods by which the heart pulse rate is predetermined by means of a sensor and stimulation is delivered in a rhythm at any time within the heart pulse rate and is synchronized with the heart pulse rate.

Such cardiosynchronized methods and apparatus can be subdivided into two classes, namely the simpulsation mode and the counterpulsation mode.

In the simpulsation mode of a cardiosynchronized electrostimulation of muscles the electric impulses are synchronized with the heart pulse rate so that the heart and the stimulated muscle are contracting at the same time, i.e. in systole phase the heart is contracting and the stimulated muscle is contracting. In the diastole phase the heart is relaxing and the muscle is relaxing.

In the counterpulsation mode of a cardiosynchronized electrostimulation of muscles the electric impulses are timed in such a way relative to the heart pulse rate, that the heart and the stimulated muscle are contracting in opposition to each other, i.e. in the systole phase the heart is contracting and the stimulated muscle is relaxing, in the diastole phase the heart is relaxing and the stimulated muscle is contracting.

Known examples of such cardiosynchronized electrophysiological methods/equipment include:

Cardiosynchronized pacemakers, anti-tachycardia pacemakers and defibrillators, which are, for example, again available from Medtronic Inc., Cardiomyostimulators, also available from Medtronic Inc., Intra-aortal balloon counterpulsation methods and apparatus, Cardiomyoplasty surgery for heart muscle conglomerates assisted by cardiosynchronized electrostimulation, External aorta counterpulsation method in which the aorta is bound by a musculo-aponeurotical graft, with its free end bissected to mobilize a sector of the aorta, as disclosed in the patent, SU 1509045 A and in the English language paper by L. V. Lapanashvili, entitled "Automuscolar System of Assisted Circulation for Surgical Correction of Cardiac Failure", published in "II Cuore", Rivista di Cardiochurgia e Cardiologia, Vol. IX, n. 1 January/February 1992, pages 5 to 27.

Pacemakers and defibrillators are well known and are inserted into the patient's body by a surgical operation. They also require replacement at regular intervals. This class of device is therefore an invasive surgical technique and indeed stimulates the heart muscles directly and does not act on the peripheral vascular system.

A cardiomyostimulator operates by taking a signal from the heart and using it to stimulate another muscle in synchronism with the heart beat.

The surgical technique used in conjunction with a cardiomyostimulator is referred to as cardiomyoplasty and is, for example, described in the book "Transformed Muscle for Cardiac Assist and Repair" edited by Ray C. J. Chiu, Ivan M. Bourgeois, Bakken Research Center Series, Volume 2, Chapter 21, pages 231 to 233.

The cardiomyoplasty procedure consists of wrapping a skeletal muscle around the heart and stimulating this wrapped around muscle in a manner synchronized with the heart contractions, i.e. in the simpulsation mode, thereby forming a heart muscle conglomerate which assists the heart pumping function. By way of example a cardiomyostimulator supplied by Medtronic Inc., as model SP1005, is a two-channel system consisting of a cardiac pacemaker channel and a myostimulation channel coordinated by a synchronization circuit. The cardiac pacemaker consists of a sensing amplifier, which monitors the intrinsic heart rate and an output stage, which paces the heart as soon as the heart rate drops below a programmed value. A cardiac event can be sensed or initiated by the device, as in a synchronized pacemaker, but furthermore it also triggers the synchronization circuit. The trigger signals are processed through a programmable divider, which allows for different heart/wrapped around muscle contraction ratios within the heart muscle conglomerate. A delay is then initiated after which the myostimulator is enabled. This sends a burst of impulses, beginning typically at the end of the R-wave and ending typically at the end of the T-wave, to the wrapped around muscle via a pair of muscular pacing leads resulting in the heart muscle conglomerate contracting in the simpulsation mode. As the name implies, cardiomyoplasty surgery is used to improve heart muscle conglomerates and is also an invasive method.

The intra-aortal balloon counterpulsation is a high-risk, complicated invasive surgical technique which is only used with terminally ill patients. It involves the insertion of a balloon into the aorta which is pumped up and evacuated in accordance with the heart rhythm so that, when inflated, the balloon generates a back-pressure wave improving blood flow through the coronary blood vessels and thus increasing the oxygen supply to the heart and hopefully improving its condition.

The external aorta counterpulsation process is also a form of myoplasty surgery and uses cardiosynchronized electrostimulation of skeletal muscles wrapped around the aorta and, when operated in the counterpulsation mode, results in an increase of coronary blood circulation in the diastolic phase, with a consequential decrease of the heart load. The above mentioned paper by Lapanashvili L. V. in "Il Cuore", reports on a 28% increase of coronary blood circulation. However, it will be understood that this is a serious invasive surgical operation only used in critical cases and therefore of limited application.

All of the above cardiosynchronized electrophysiological methods which use stimulation in the simpulsation mode do not result in a significant change of the heart load when compared with the heart load of the same person without stimulation. The counterpulsation methods hitherto described all involve invasive surgery. There are, however, some further counterpulsation methods referred to in the literature which are essentially non-invasive and these are based on so-called pneumatic boot therapies.

Such pneumatic boots or compression boots, for example the boot made by the Circulator Boot Corporation, do not use electrostimulation, but instead apply pressure pulsations pneumatically to the lower leg of the patient. More specifically this equipment applies pneumatic compression to the patient's lower leg and this application of pressure is synchronized with the heart rhythm. The Circular Boot product is known to be a non-invasive cardiosynchronized pneumatic compression boot which pneumatically compresses chosen portions of body extremities, for example the lower leg, in either the simpulsation or counterpulsation mode. In the latter mode the Circulator Boot is timed to release the leg in anticipation of the cardiac systole and the primary intention is to improve arterial flow in the leg.

Indications for which the Circulator Boot can provide treatment are poor arterial flow in the leg, diabetes, arterial insufficiencies, venous diseases, lymphedema, etc.

It is stated by the manufacturers, on their home page as of Jun. 6, 1999, that Circulator Boot therapy increases stroke volume by decreasing afterload while at the same time decreasing heart work and maintaining or increasing coronary perfusion. The fact that the Circulator Boot has some effect on the heart can be seen from the statements on the cited home page, where it is, for example, stated that "anecdotal measurements providing evidence for cardiac benefit have included: reduction of the loudness of mitral insufficiency murmurs; widening of the peripheral pulse tracing with leg pumping during systole; narrowing of the tracing with end-diastolic pumping; raising the dicrotic notch with systolic pumping and lowering it with end-diastolic pumping and, in patients with a SwannGanz catheter in place, lowering wedge pressure and increasing cardiac output".

Finally, reference is made to the Georgian patent 366 of the present inventor L. V. Lapanashvili which describes the stimulation of muscles in a non-invasive external technique in the simpulsation and counterpulsation mode. This document discusses stimulation of muscles on the chest, near the heart, in the simpulsation mode and states that "it unloads the heart and enables even chest muscles located near the heart to be stimulated". Thus, here, heart unloading has been achieved by stimulating the chest muscle in the simpulsation mode. The patent states that the regime of counterpulsation is most often used, but when electrodes are placed on the chest, i.e. near the heart, the regime of simpulsation is used.

A principal object of the present invention is to provide an almost universally applicable method and apparatus by which a substantial degree of heart unloading can be achieved by appropriate non-invasive or invasive stimulation of the patient which can be applied without practical time limitation and in particular without any restrictions of the muscles to be stimulated, with the exception of the heart muscle itself.

Moreover it is an object of the present invention to provide a method and apparatus which is entirely harmless and which can be used not only for the prevention and rehabilitation of coronary infarct and heart insufficiency, but also for neuromuscular or direct muscle stimulation, resulting in visible or non-visible muscle contractions, for muscle power or endurance development, body shaping, lypolysis treatment and the like.

It is a further object of the present invention to provide a method and apparatus capable of use for neuro-neuromusclar or direct muscular anti-pain stimulation including trancutaneous electrical nerve stimulation (frequently called TENS) as well as for many other applications of aesthetic and curative medicine.

In order to satisfy this object there is provided, in accordance with the invention, a method of treating a mammal or other living organism having a heart and a peripheral vascular system, in particular a mammal, and especially a human being, to achieve a heart load reduction, said organism having a pulse rate and a systolic pressure resulting from the action of the heart, the method comprising the steps of:

measuring the heart rhythm, producing pressure pulsations in the peripheral vascular system by a non-invasive method in synchronization with the heart rhythm in the counterpulsation mode and varying at least one parameter of said pressure pulsations to produce an optimized reduction of at least one of said pulse rate and said systolic pressure and hereby a net reduction in said heart load, said heart load being a function of said pulse rate and said systolic pressure.

A corresponding apparatus for carrying out the method comprises means for measuring the heart rhythm, means for producing pressure pulsations in the peripheral vascular system by a non-invasive or invasive method in synchronization with the heart rhythm in the counterpulsation mode and means for varying at least one parameter of such pressure pulsations to produce an optimized reduction of at least one of said pulse rate and said systolic pressure and hereby a net reduction in said heart load.

The invention is based on the wholly surprising discovery that it is possible, by optimizing the pressure pulsations produced in the peripheral vascular system of a patient by a non-invasive method in synchronization with the heart rhythm in the counterpulsation mode, to secure an optimized reduction in the patient's pulse rate and hereby a significant, and indeed highly significant, net reduction in the heart load. This is a particularly surprising discovery because it is not at all evident that a totally non-invasive stimulation of, for example, a leg muscle, on only one of the many peripheral branches of the cardiovascular tree would ever be able to increase coronary blood flow and reduce heart load by a significant amount. Indeed it is totally surprising that the degree of reduction of the heart load achieved in tests is similar to that achieved by the risky, fully invasive, extra-aortal muscular flap wrapped around the aorta assisted by electrostimulation. It will be appreciated that these latter techniques act directly at a location on the aorta, the main trunk of the cardiovascular tree, whereas the invention acts externally on just one of many branches of the peripheral vascular system.

More specifically it has been found that, by correctly setting the pressure pulsations for the individual patient, a type of resonant phenomena arises which can be exploited, so that a small perturbation of the peripheral vascular system leads to an optimized reduction in the pulse rate and through this a net reduction in the heart load. It is particularly favorable that the reduction in the pulse rate is also accompanied by a reduction in the systolic pressure so that a very pronounced effect with respect to the heart load is achieved by just a small perturbation of only one peripheral branch of the cardiovascular tree. With patients having normal blood pressure there is only a small reduction in blood pressure, but a large reduction in pulse rate. For patients with high blood pressure the reduction in blood pressure is pronounced, but the reduction in heart rate less so. The method and apparatus of the invention can namely be used for the simulation of any smooth or skeletal muscle in the body, other than the heart muscle, and will result in the beneficial effect of significant heart unloading as described above.

Looked at another way, the invention enables the implementation of a method of achieving a heart load reduction in a living body having a heart, such as a mammal, and especially a human being, by measuring the heart rhythm and by producing pressure pulsations in the peripheral vascular system in synchronization with the heart rhythm in the counterpulsation mode to produce an optimized reduction in the pulse rate and hereby a net reduction in the heart load, the heart load being a function of the pulse rate and the systolic pressure.

In distinction to a pneumatic boot, the apparatus of the present invention can be made extremely light, compact and portable and can be worn by the user in the course of normal daily life without any significant restrictions on the patient's mobility and style of living. The means for measuring the heart rhythm can easily comprise a non-invasive sensor at some discrete position on the patient's body, since the sensor only needs to provide a basic signal enabling synchronization of the stimulation apparatus in the counterpulsation mode.

To ensure the mobility of the patient, this stimulation apparatus is conveniently an electrostimulation apparatus which can be powered by a small battery carried by the patient. The energy requirement is not excessively high because, as noted above, the apparatus basically only imposes a perturbation on the peripheral vascular system of the patient and the effect of this perturbation is effectively enhanced by a phenomenon which is not understood in full, but which can be likened to resonant phenomenon where a small perturbation results in a large effect.

This resonant phenomena can be explained as follows:

A dynamic change of pressure level during diastole arises from the blood expelled from the heart and the partial or total reflection of two different pressure waves, propagating simultaneously from different locations in opposite directions. The blood expelled from the heart originates from the contraction of the heart during systole and involves a blood flow rate less than 1 meter per second.

The first pressure wave considered during diastole is induced by the blood ejected from the heart, i.e. the opening of the heart valve and the resulting pressure wave propagates at a much higher speed—typically some 4 to 7 meters per second—from the heart valve through the arterial system. This first pressure wave is partially reflected at an induced muscle contraction. The not reflected part of the pressure wave propagates through the capillary and arterial blood vessels of the muscle into the venous system. The reflected pressure wave, however, propagates in the arterial system back to the heart and is then reflected at the now closed heart valve. It then again propagates downstream and again upstream etc. This reflection of pressure wave propagation continues as long as the muscle is being contracted, i.e. as long as the passage of the blood flow is being partially obstructed by the squeezing of the blood vessels resulting from the muscle contraction.

The second pressure wave is the pressure wave induced by the beginning of the muscle contraction at the periphery which is practically identical in time with the start of the stimulating pulses. This muscle contraction squeezes the capillary and arterial blood vessels in the muscle and expels part of the blood backwards into the arterial system and partially forward into the venous system, thus inducing pressure wave propagation at a higher speed than the normal pressure wave propagating speed of 4 to 7 meters per second. The speed increase of this second pressure wave propagation is proportional to the strength of the muscle contraction. This second pressure wave propagates in the arterial system back to the heart and is reflected at the closed heart valve. It then propagates downstream at normal pulse pressure propagation speed and again upstream and so on.

This reflection of pressure wave propagation continues as long as the muscle is contracted, i.e. as long as the passage of the blood flow is being partially obstructed by the squeezing of the blood vessels resulting from the muscle contraction.

By optimizing the timing of the muscle contraction relative to the pumping of the heart through the choice of a suitable delay it is possible to achieve a type of constructive interference between the pressure waves leading to an increase in pressure in the aorta in the form of a pressure hump just after opening of the heart valve and this increase in pressure corresponds to a resonant phenomena which increases the flow through the coronary arteries and is followed by a pressure reduction resulting in a lowered presystolic pressure of the heart. This is one element which contributes to the heart unloading.

Investigations have shown that the delay which produces good results, i.e. the suitable delay referred to above can vary within a relatively wide window for different persons and manners of stimulation. More specifically, it has been found that the suitable delay for resultant heart unloading through pressure increase due to muscle contraction lies in a window between 5% of the length of the R-R path before the end of the T-wave and 45% of the length of the R-R path after the end of the T-wave. That is to say, in an embodiment with electrical stimulation, the stimulation has to start at a time within this window to produce the desired effect, the precise timing can be optimized for different individuals.

For this reason the method of the invention can be referred to as a cardioresonance stimulation method and apparatus.

In addition to electrical stimulation the present invention can, however, also be realized by using other ways of producing pressure pulsations in the peripheral vascular system, such as the use of a pressure pad contacting or encircling any skeletal or smooth muscle of the organism belonging to the peripheral vascular system. Although a pneumatic boot could be used for this purpose, it is also possible to use a much smaller simple pressure pad in order to realize the present invention because the function of the pneumatic stimulation is simply to produce a small perturbation in the peripheral vascular system rather than to squeeze the whole lower leg to effectively pump blood through it.

Accordingly, a pneumatic or hydraulic pressure pad for use in accordance with the invention can be made small and light and thus used during the normal daily life of the patient, rather than only being capable of being used when the patient is at rest, this being a serious disadvantage of a pneumatic boot, particularly since it restricts the length of each treatment. In contrast the apparatus of the present invention can be used for days on end if desired.

Other ways of producing pressure fluctuations in the peripheral vascular system can comprise treating the patient by impulses of light or by means of a pulsating oxygen supply, or indeed a pulsating $CO_2$ supply. Laser excitement treatments, electrically energized acupuncture treatments and acoustic treatments can also be considered as ways of producing the required pressure pulsations in the peripheral vascular system. In each case it is important that the stimulation is applied in a counterpulsation mode and that the parameters of the stimulation are appropriately selected for the patient, such parameters comprising:

the impulse delay before the start of counterpulsation, said impulse delay being the time difference between the Q-wave end of a QRS heart rhythm signal and the start of a train of stimulating impulses generating pressure pulsation, the train duration, i.e. the time between the start and end of a train of stimulating impulses within one heart rhythm, the frequency of the impulses forming a train of stimulating impulses generating pressure pulsation, the impulse width, i.e. the time between the start and the end of one stimulating impulse of each said train, the amplitude of stimulating impulses generating pressure pulsation, the impulse form, being the geometric form of the stimulating impulse resulting when an amplitude of the impulse is displayed over a full impulse duration, the impulse mode, being the relationship between positive and negative half cycles of each said stimulating impulse.

The apparatus of the present invention can also be used in conjunction with a long term ECG, for example a 12-channel ECG, enabling medical practitioners to obtain a detailed insight into the patient's response to the treatment over a longer period of time. Such long-term ECGs, again in the form of portable apparatus are known per se and usually involve the temporary storage of data, a facility for compression of the stored data and a facility for read-out at regular intervals, for example once per day.

The cardioresonance electrostimulation apparatus of the invention results in accompanying effects in all body systems influenced by dynamic changes in the cardiovascular system. I.e., on using the invention it is found that reactions result in all body systems of the living body, which are triggered by dynamic changes in the cardiovascular system by the cardioresonance phenomena resulting from the use of the invention.

The reactions in these other body systems can not yet be fully explained, however results have been observed in various body systems and these body systems are well known to be influenced by dynamic changes in the cardiovascular system. Some of the observed results are measured facts, some of them are perceptions and feelings reported by the probates. However, these observed results allow the assumption, that similar physical/physiological/biochemical reactions take place in these systems interlinked with the cardiovascular system. These observed results include observations which are partially known from asynchronous electrostimulation, however, with cardioresonance electrostimulation these reactions are more pronounced due to the cardioresonance phenomena The observed improvements include:

increased muscular endurance, power and mass intensified regional lipolysis by increased metabolism reduction of pain in body support and motion system (bone, nerves and muscles working together) e.g. by strengthening of selective leg muscles and thereby unloading knee joints by changing the loading angle, whereby the loading force in joints are applied to other areas, resulting in reduction of pain caused, for example, by arthrosis, or by osteochondrosis whereby strengthening of selective back muscles will reduce pain caused by backache or radiculitis and ischiasis improved quality of skin, becoming smooth & elastic by increased regional blood circulation increased immunological resistance, e.g. reduction and elimination of chronic inflammation was measured improved mental & psychological condition, e.g. cheerfulness, mood improvement by increased endorphin production etc.

normalization of sleep increased overall fitness, wellness and working capabilities & efficiency feeling light when walking, etc.

The invention can, for example, be used to achieve benefits from one or more fields selected from the following group:

promotion of fitness and wellness, physical training for sport, aesthetic medicine, including any kind of desired body shaping and/or tissue changes, e.g. due to body fat burning (lipolysis), fluid drainage and tissue and muscle growth and/or reduction as well as associated skin changes, curative medicine, including invasive and non-invasive methods, cosmic medicine.

Furthermore, the invention can be used in the field of curative medicine, or for the prevention of disease in any of more of the following fields:

for anesthesiology, for example to reduce the risk of acute heart failure, for cardiology, for example to remedy tachycardia, ischemic heart disease, cardiomyopathy, hypertension, heart failure, valvular pathology, for angiology, for example for lymph-venous and arterial insufficiencies, for orthopaedy and neurology, for example to remedy hypotrophy and atrophy of muscles, for pain reduction including anti-pain TENS-treatment for any kind of pathology in the body support and motion system of a human being, for example for osteochondrosis, for urology and proctology, for example for sphincter insufficiencies, for gynaecology and sexology, for example for the treatment of dilatatio vaginae, descendus uteri, adnexitis, amenorea, frigidity, for endocrinology, for example for adipositas partialis, hypomastia, for surgery, for example for diastasis musculi recti abdominis, decubiras, for cosmic medicine, for example to preserve muscle tone of astronauts.

A particularly important aspect of the present invention is the way the time, i.e. the impulse delay, at which stimulation is applied to the living organism by the input system is adjusted to compensate for the reduction in pulse rate resulting from the treatment which has been found to enhance the cardioresonance phenomenon underlying the present invention.

It should be noted that it is, however, conceivable that the invention can be realized without this adjustment. For example, the time, i.e. the impulse delay, at which the stimulating impulses are applied to the living organism or patient could initially be delayed beyond the end of each T-wave, so that as the patient's heart rate drops as a result of the stimulation and the end of the T-wave occurs later, due to the increased duration of each heart beat, the stimulating impulses ultimately coincide with the end of the T-wave at the lower heart beat.

There are two basic ways in which the end of the T-wave can be established from the point of view of triggering each new train of stimulating impulses. In the first case the end of the T-wave can be directly detected, for example, from an electrocardiogram and the trains of pulses triggered as soon as the end of the T-wave has been detected.

Alternatively, other reference points on the electrocardiogram can be recognized, for example the ends of the Q-waves or the R-peaks, and a suitable delay to the end of each respective T-wave can then be calculated, since the length of the Q-T path has a known fixed relationship to the length of the R-R path. The trains of stimulating impulses are then triggered at the calculated ends of the T-waves.

The duration of each train of stimulating impulses is preferably selected to amount to 10 to 25% of a T-Q diastole duration, for example of the T-Q diastole duration of a normal human being at rest. This leads to a duration of pressure pulsations in the peripheral vascular system for each diastole phase of between 5 and 40% of the length of the R-R path. If mechanical stimulation is used, for example, a pressure pad, then the duration of the applied pressure corresponds to the value of 5% to 40% of the R-R path and is subsequently equal to the muscle contraction.

Further advantageous embodiments of the invention and preferred apparatus for carrying out the method of the invention are set forth in the subordinate claims incorporated herein by reference.

Figure 5:
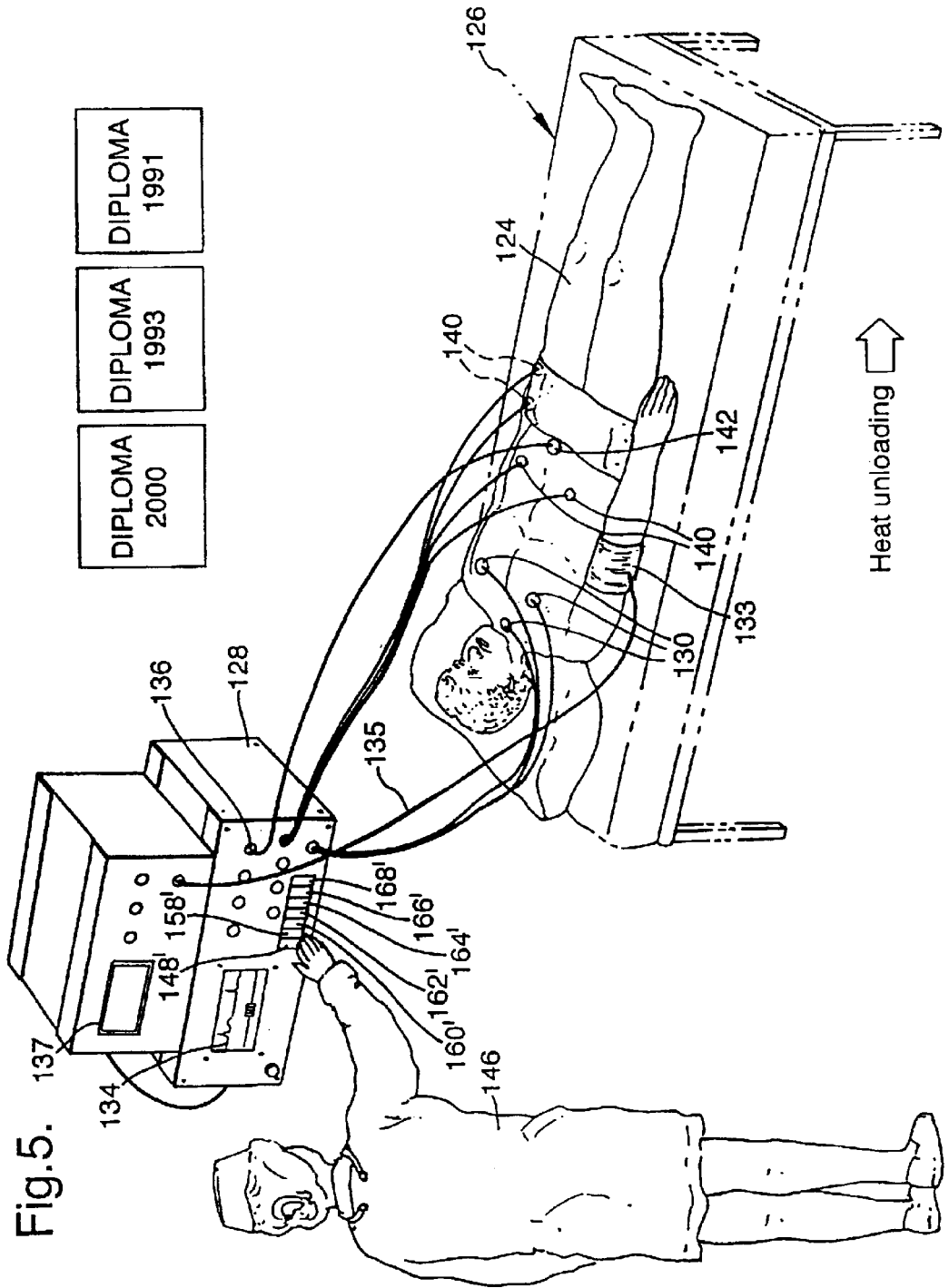
Figure 6:
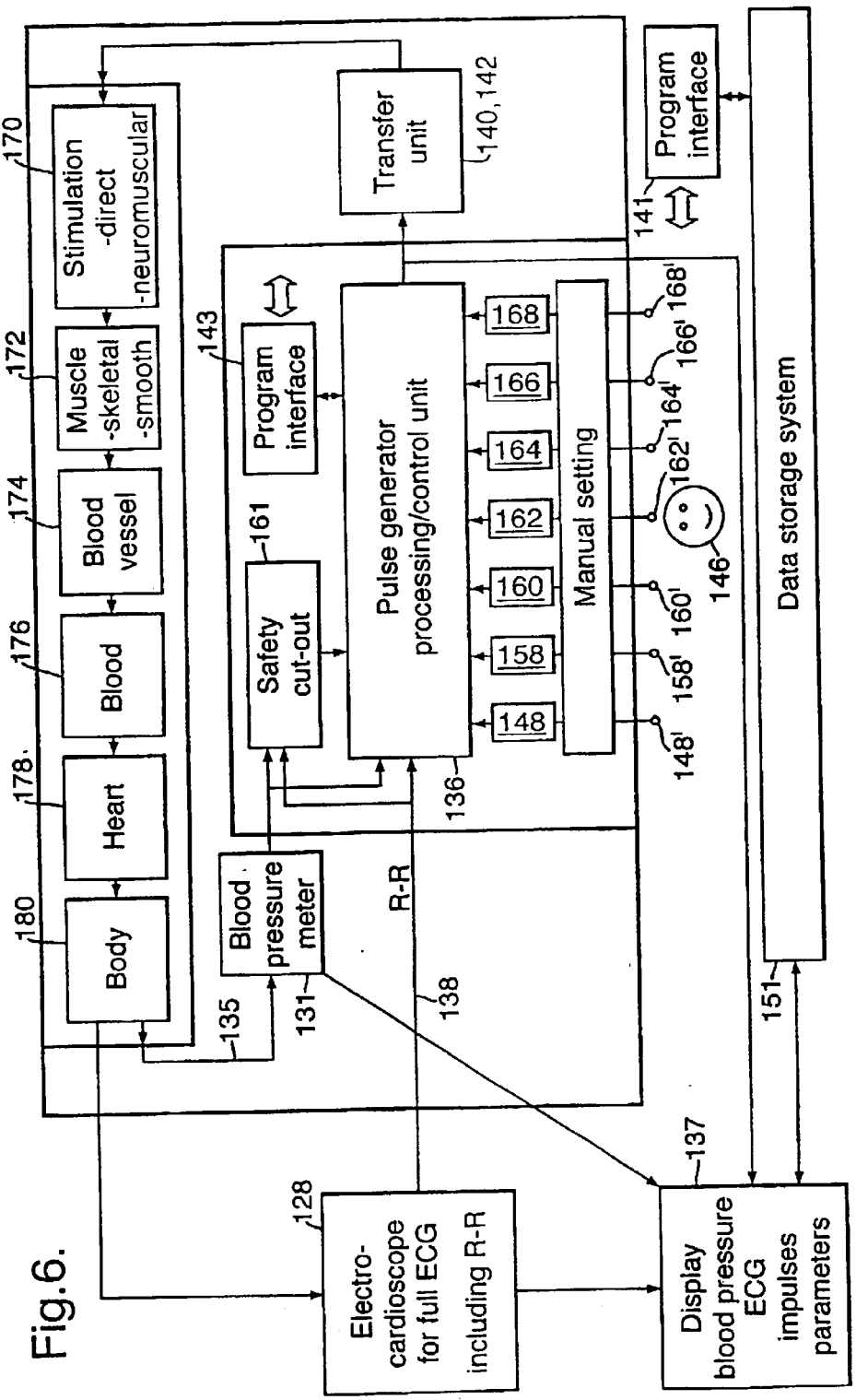
Figure 7:
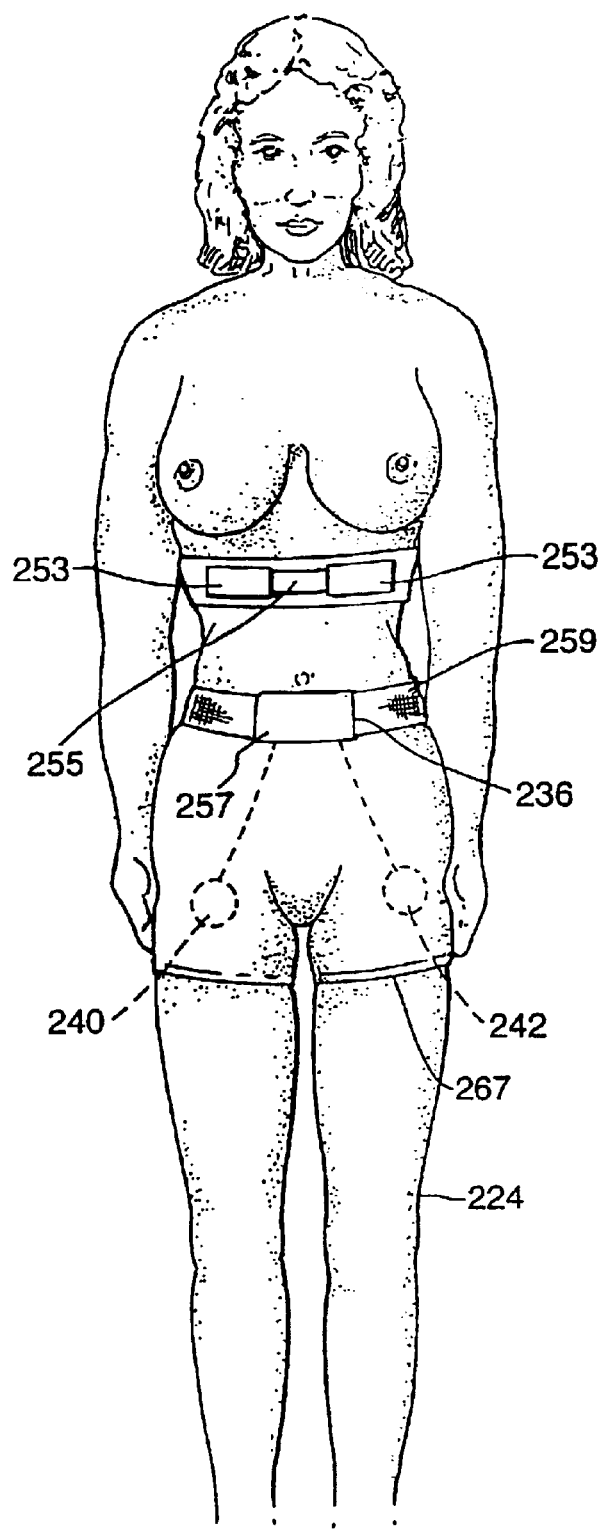
Figure 8:
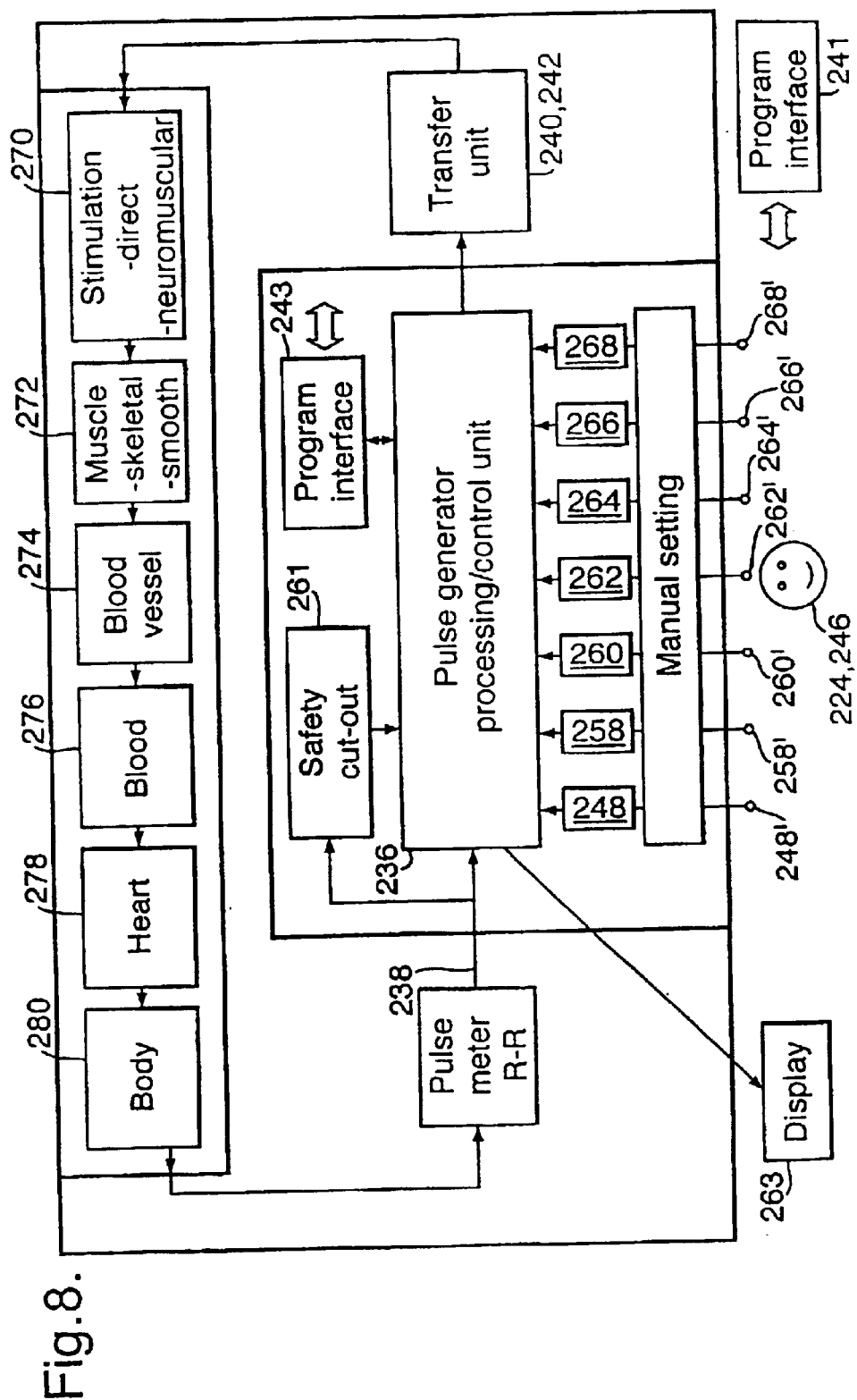
Figure 9:
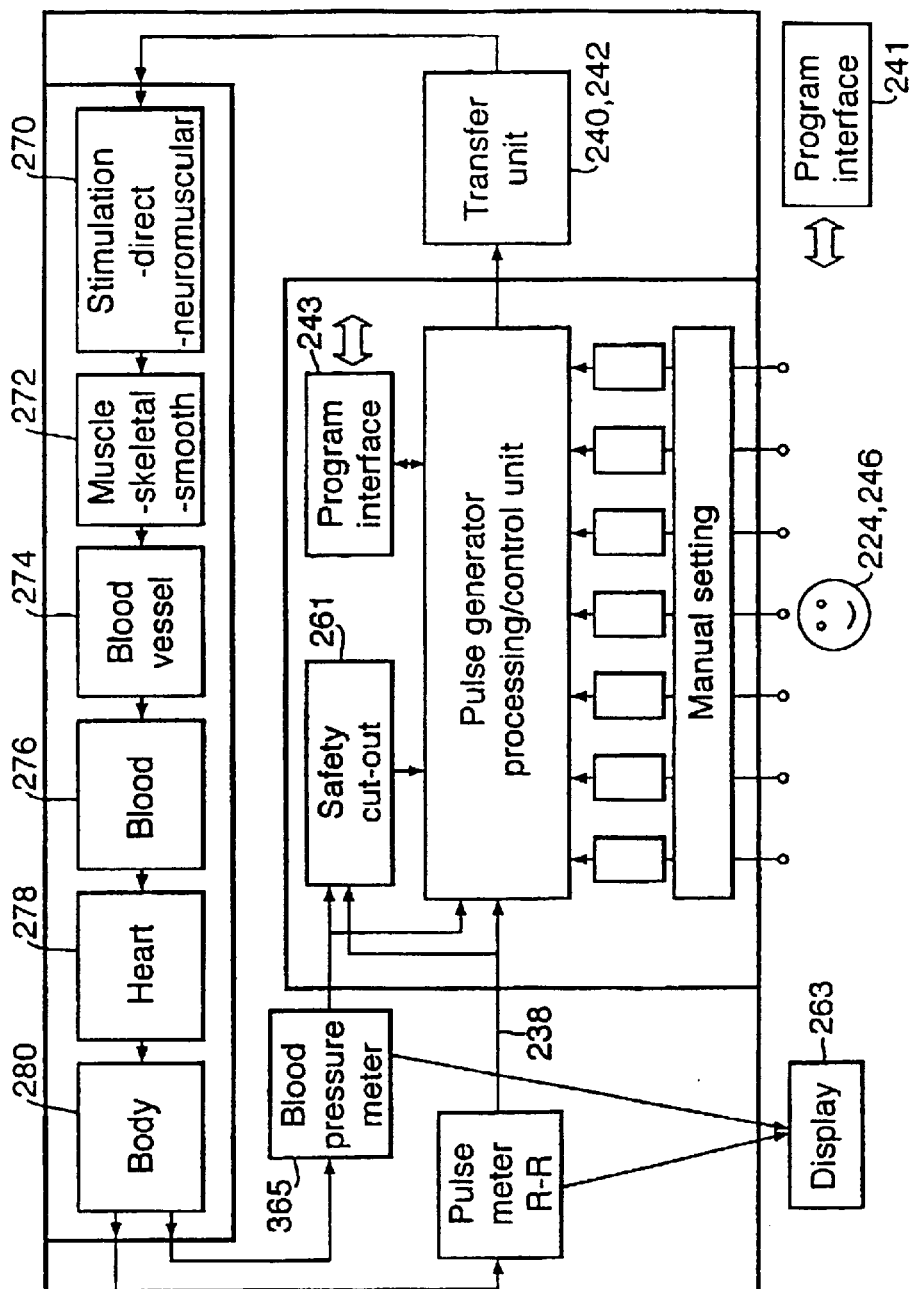
Figure 10:
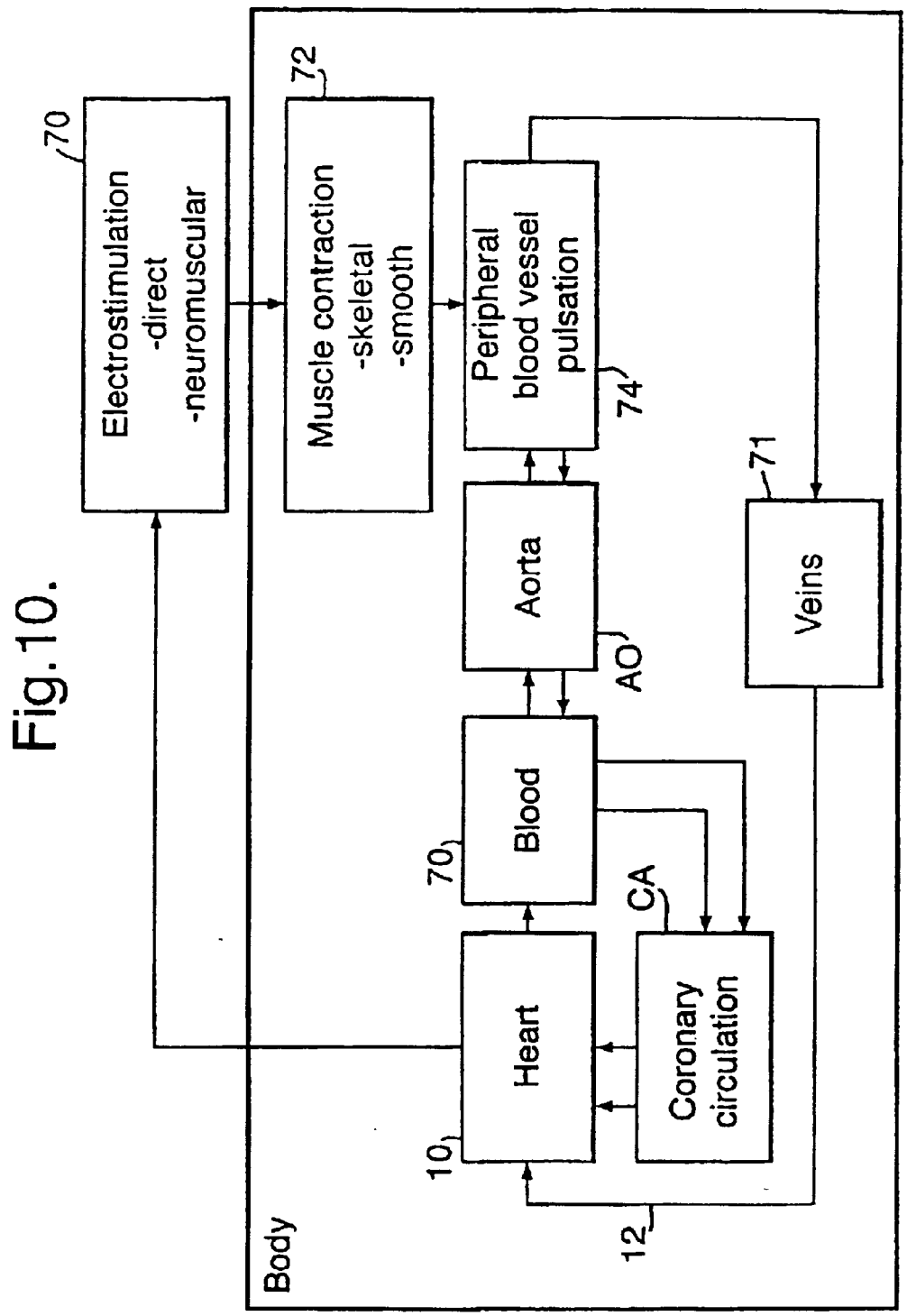
Figure 12B:
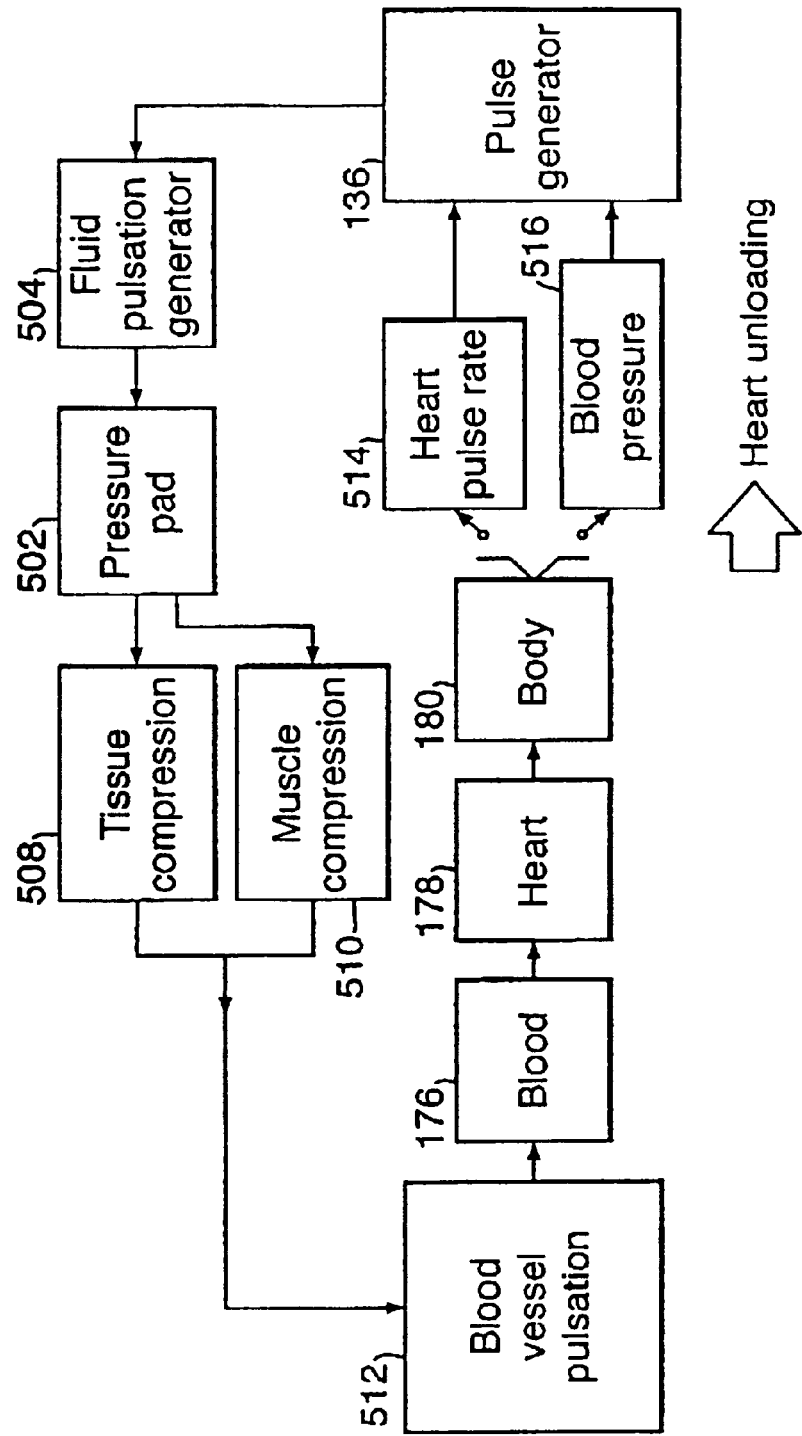
Figure 13A:
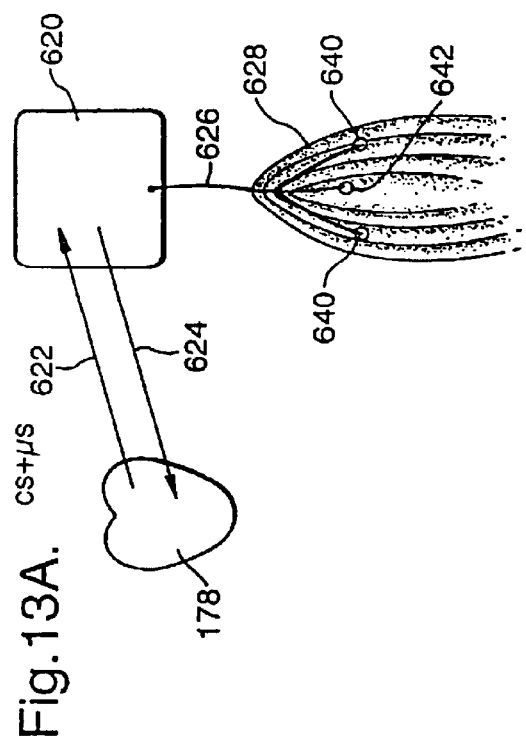
Figure 13B:
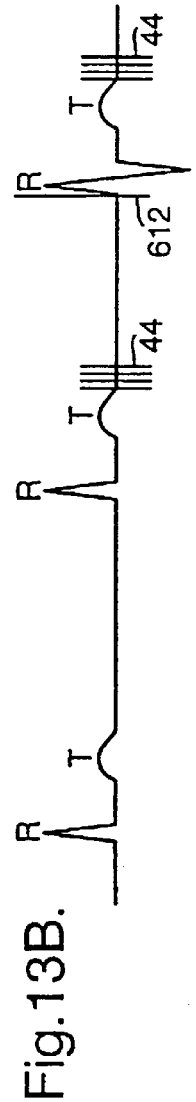
Figure 13C:
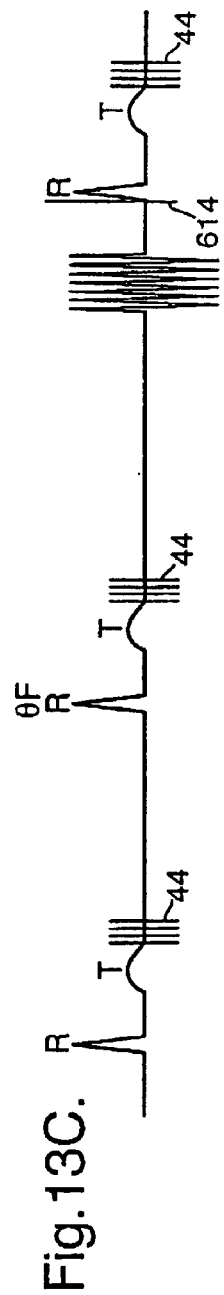
Figure 14:
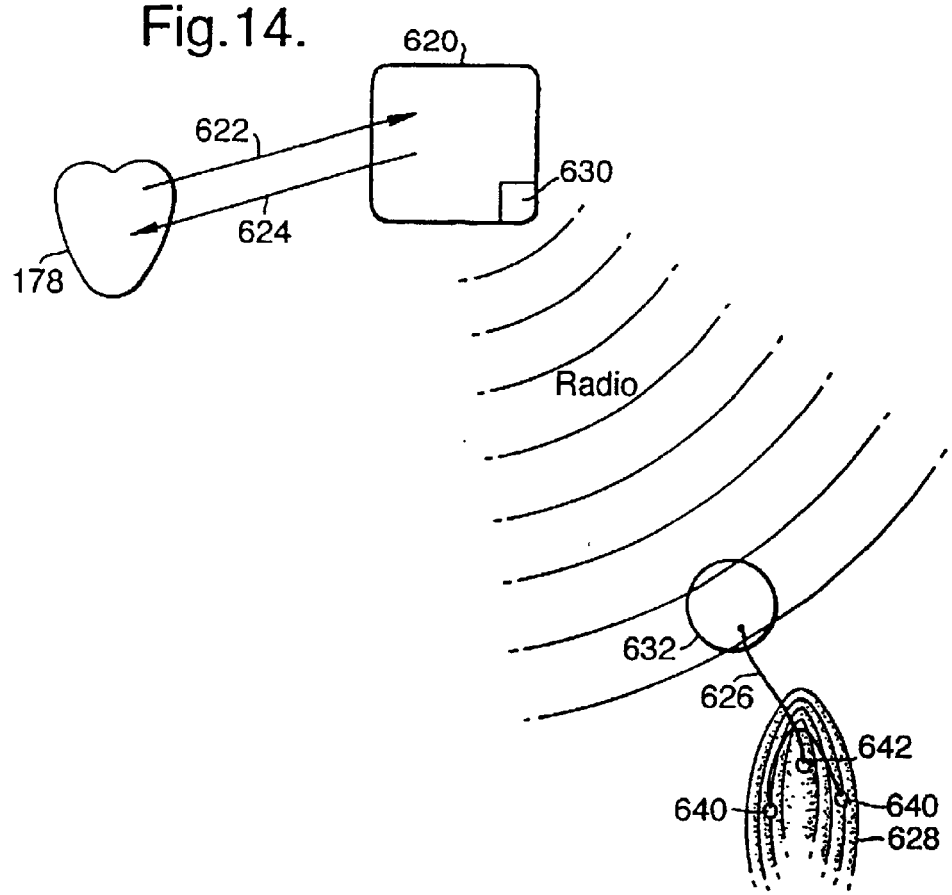
Figure 15:
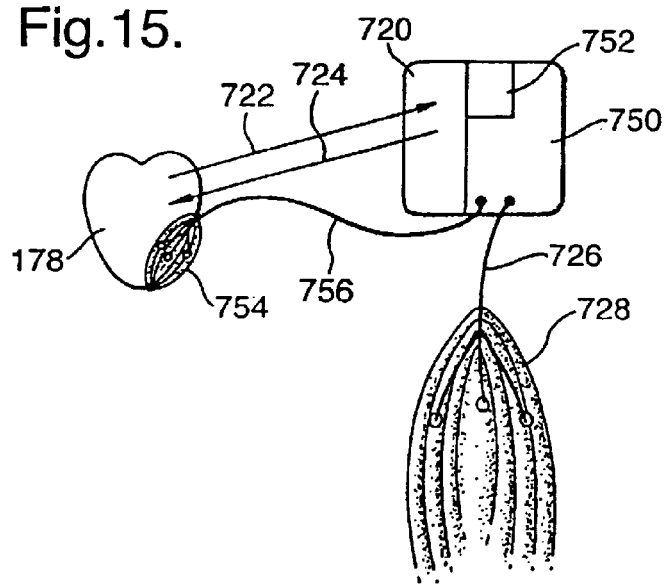
Figure 16:
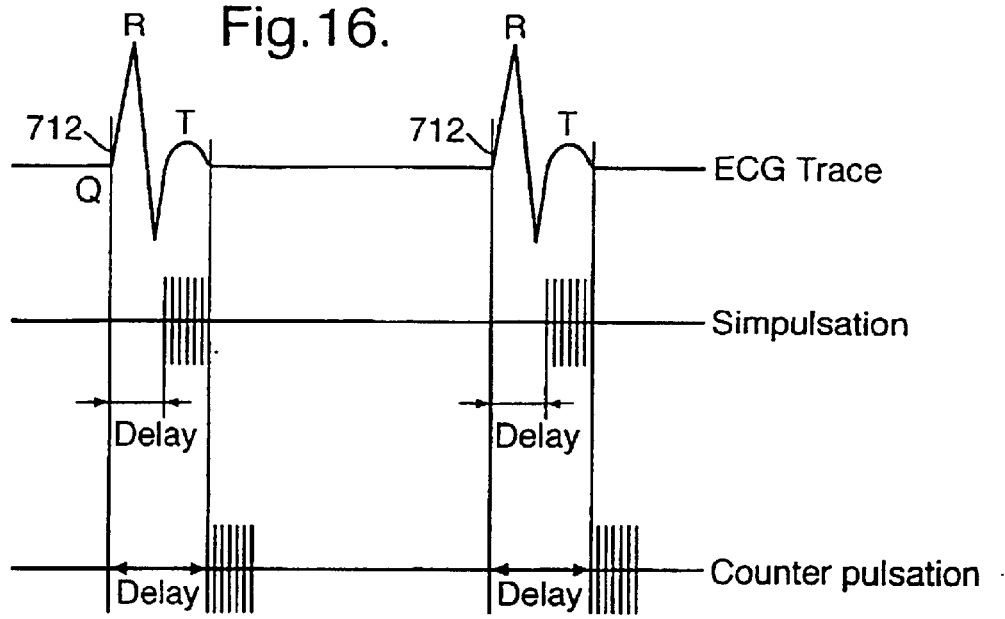
Figure 17:
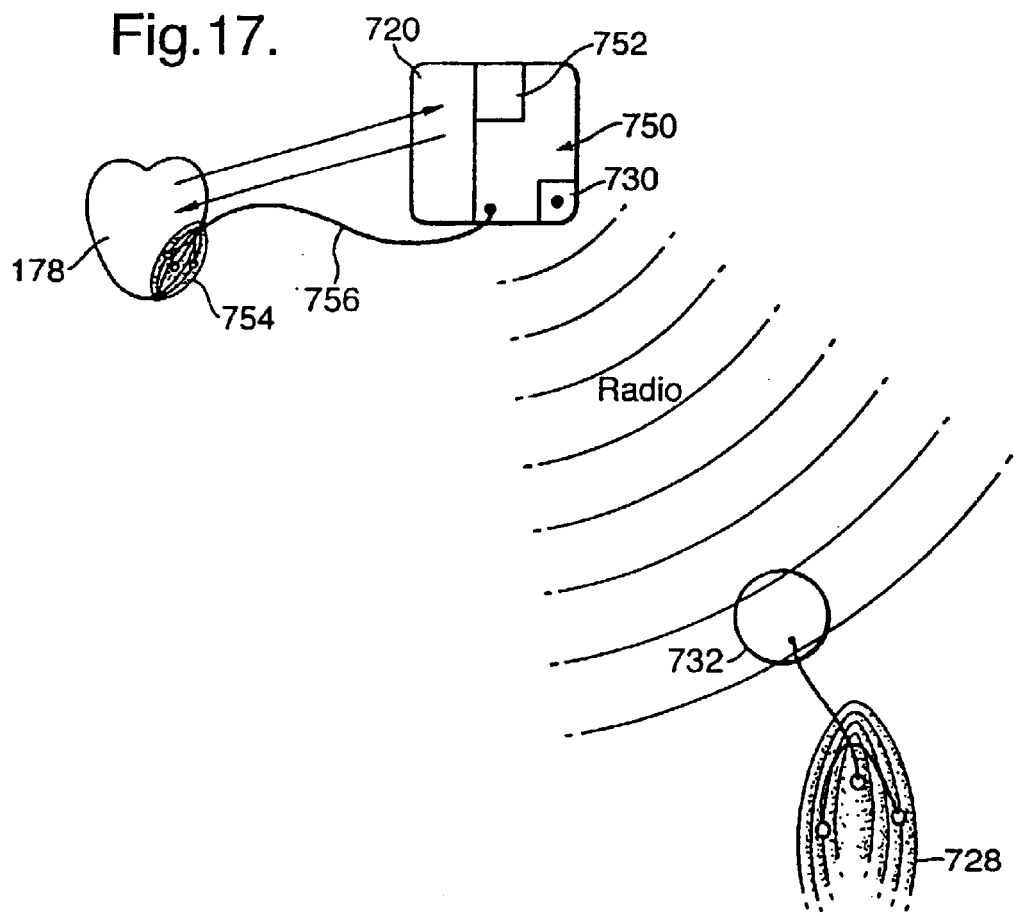
Figure 18:
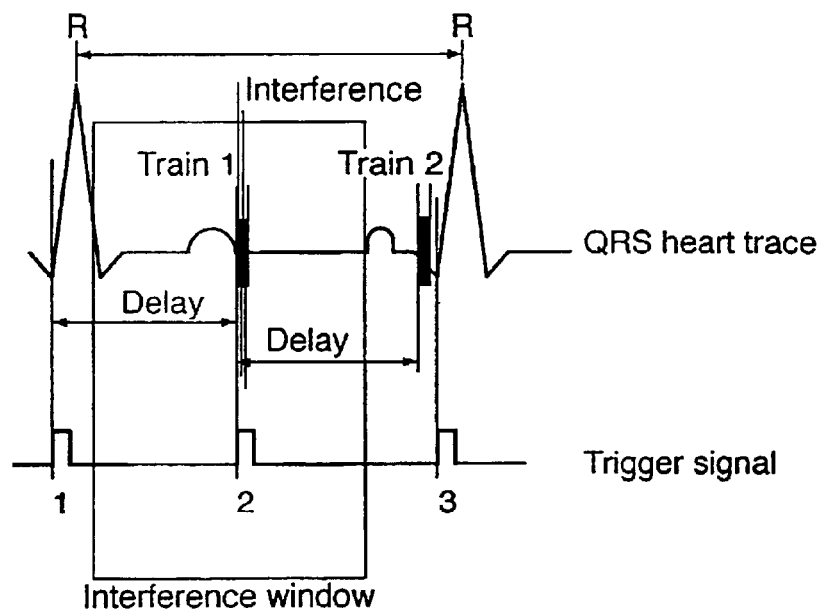
Figure 19:
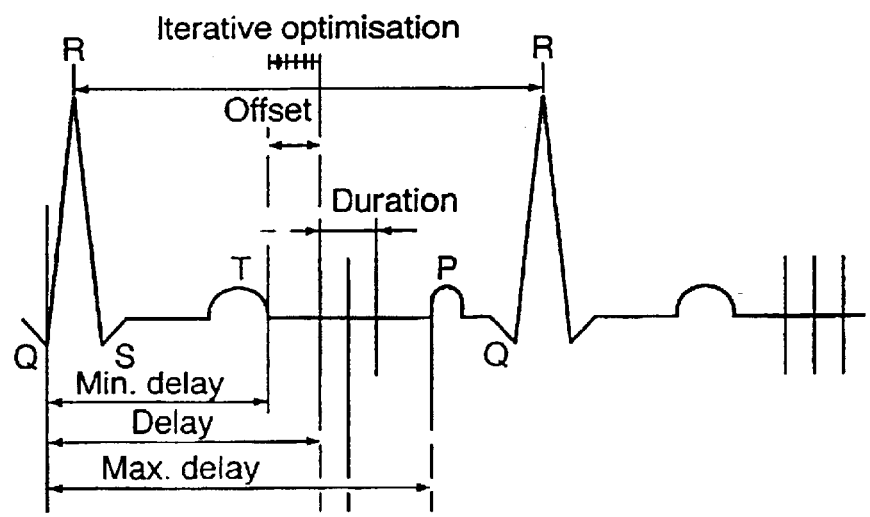

The present invention will now be explained in more detail in the following with reference to preferred embodiments and to the accompanying drawings in which are shown:

FIG. 1A a schematic diagram illustrating a typical electrocardiogram,

FIG. 1B a schematic diagram of the human heart,

FIG. 1C an enlarged view of the aorta at the junction with the heart and with the coronary arteries, FIG. 2A a schematic diagram of a first variant of an apparatus for applying electrostimulation in accordance with the present invention, FIG. 2B a graph illustrating the terminology used to describe a biphasic rectangular impulse, FIG. 2C a graph illustrating the timing of the pulses applied to a patient in the counterpulsation mode to achieve cardioresonance in accordance with the invention, FIG. 3 a set of diagrams showing the effect of the method and apparatus of the invention on the operation of the heart of a patient, FIG. 4 a block circuit diagram illustrating the operation of the apparatus of the variant of FIG. 2A, FIG. 5 a second variant of an apparatus in accordance with the invention for applying electrostimulation to a patient, using the pulse rate and/or a blood pressure meter as an input signal, FIG. 6 a block circuit diagram illustrating the operation of the apparatus of FIG. 5, FIG. 7 a diagram illustrating a treatment system which can be worn by a patient while leading a normal life, FIG. 8 a block circuit diagram illustrating the operation of the apparatus of FIG. 7, FIG. 9 a block circuit diagram similar to FIG. 8 showing a further development thereof, using the pulse rate and/or a blood pressure meter as an input signal, FIG. 10 a block circuit diagram summarizing the effect the method and apparatus of the invention have on the human body, FIG. 11 a diagram explaining the various types of muscular stimulation that are possible when using the present invention, FIG. 12A a diagram illustrating an alternative method of stimulating a patient in accordance with the present invention by a pressure pad, FIG. 12B a flow diagram illustrating the operation of the apparatus of FIG. 12A, FIG. 13A a diagram illustrating the combination of the invention with a cardiostimulator, FIG. 13B a diagram illustrating the function of the invention in combination with a pacemaker, FIG. 13C a diagram illustrating the function of the invention in combination with a defibrillator, FIG. 14 an alternative combination to that of FIG. 13A, FIG. 15 a diagram illustrating the function of the invention in combination with a cardiomyostimulator, FIG. 16 a diagram illustrating the operation of the combined equipment of FIG. 15, FIG. 17 a diagram showing an alternative to the combination of FIG. 15, FIG. 18 a diagram illustrating a preferred embodiment with an interference window, and FIG. 19 a diagram illustrating methods of optimizing the timing of the stimulation signals.

Turning now to FIGS. 1A, 1B and 1C, a brief description of the normal operation of the human heart be given in order to facilitate an understanding of the present invention.

The heart 10 shown in FIG. 1B has four chambers, namely the right atrium RA, the right ventricle RV, the left ventricle LV, and the left atrium LA. Venous blood returning to the heart flows into the right atrium, then into the right ventricle and passes to the lungs via the pulmonary artery PA. In the lungs the blood picks up oxygen and returns to the left atrium LA, as indicated by the arrow 14. From there, the oxygenated blood passes into the left ventricle, and then into the aorta AO where it starts on its journey through the so-called big circulation around the body. The circulation from the right ventricle to the lungs and then to the left atrium is called the minor circulation.

The operation of the heart is associated with electrical signals, which are shown on the electrocardiogram of FIG. 1A. The point P signifies the contraction of the two atriums RA and LA, which pushes blood into the respective ventricles RV and LV via the respective valves 16 and 18, which act as non-return valves. The section of the electrocardiogram starting with Q and ending with T is referred to as the systole and represents the ventricle contraction which serves to expel blood from the right ventricle into the pulmonary artery, and from the left ventricle into the aorta. During this contraction, the valves 16 and 18 are closed to prevent reverse flow into the right atrium and left atrium. The section TQ is referred to as the diastole, meaning the relaxation or expansion of the ventricles. The heart is supplied with oxygenated blood via the coronary arteries CA, which branch off from the aorta just upstream of the valves 20, 22, which close to prevent blood returning from the aorta to the left ventricle during the diastolic phase. Clearly the heart, itself a muscle, must be supplied with oxygenated blood to keep the muscles working. The heart is supplied with this oxygenated blood via the coronary arteries CA during diastole. At T the valves 20, 22 of the aorta AO are closed and at this time the blood pressure in the aorta causes blood to enter the coronary arteries CA. Accordingly, an increase of the pressure in the aorta AO during diastole favors the coronary arteries.

As will be seen from the following, one of the important results of the present invention is a small increase in pressure in the aorta during diastole and this has been found to have a profound effect on the operation of the heart muscle.

FIG. 2A shows an illustration of a basic apparatus which has been used for the testing of the present invention and which clearly also represents a perfectly viable apparatus for practicing the invention, although a whole variety of further improvements and developments are possible, as will be described later.

As shown in FIG. 2A, a patient 24 is shown lying on a bed 26 and is connected to an electrocardioscope 28 via, in this embodiment, three sensing electrodes 30, which enable the electrocardioscope to show the ECG trace 32 for the particular patient 24 on the display 34. From the information available to the electrocardioscope through the three electrodes 30, a signal is extracted corresponding to the repetition frequency of the path R-R of the ECG trace of FIG. 1A. That is to say, this signal represents the frequency at which the patient's heart beats, i.e. his pulse rate.

This signal is fed to a pulse generator 36 via a line 38 which is not shown in FIG. 2A but which is schematically illustrated in the diagram of FIG. 4 relating to the operation of the apparatus of FIG. 2A. The pulse generator 36 delivers a train of biphasic rectangular pulses to the patient 24 via the active electrodes 40, of which four are shown in FIG. 2A.

The further electrode 42 is a neutral electrode necessary to complete the circuit. As illustrated in FIG. 2C the train of pulses 44 is triggered once per cycle of a patient's heart and is timed to coincide with the end of the T-phase of the ECG. The train of pulses 44 is also shown on the display 34 of the ECG, which enables the operator 46 to see the phase relationship between the train of pulses 44 and the electrocardiogram 34.

From the joint display of the ECG and the train of pulses 44 on the screen 34 of the electrocardioscope, the operator 46 can see whether the train of pulses has the appropriate delay relative to the Q-wave to secure the cardioresonance desired in accordance with the invention.

As noted earlier, the train of pulses is preferably set to start at the end of the T-wave. The operator 46 is able to adjust the phase for-the start of each train of pulses, i.e. the delay, so that it coincides with the end of the T-wave. This is one manual input into the pulse generator indicated at 48 in FIGS. 2A and 4.

Before discussing the effect the train of pulses 44 applied to the patient has, it is appropriate to discuss the terminology used in this specification with respect to the pulses generated by the input system comprising the pulse generator 36 and the electrodes 40, 42.

The basic output of the pulse generator 36 is shown in FIG. 2B. It can be seen that the train of pulses comprises a plurality of so-called biphasic, rectangular impulses. Each biphasic rectangular impulse has a rectangular positive half pulse 50, and a rectangular negative half pulse 52 immediately following the positive half pulse, so that the impulse width is determined by the width of 50 plus the width of 52. The biphasic impulse 50, 52 of FIG. 2B is then followed by an interval and is then followed by a second biphasic impulse indicated as 50', 52' in FIG. 2B. The distance between sequential positive half waves 50, 50' of the biphasic pulses determines the pulse repetition frequency of the signal. During the interval between sequential biphasic pulses and during the intervals between sequential trains of biphasic pulses, the voltage applied to the electrodes 40 is zero, i.e. the same as the voltage at the neutral electrode 42, so that no stimulation of the patient occurs. This zero voltage is indicated by 54 in the diagram of FIG. 2B. It will be noted that instead of applying voltages to the electrodes, currents can be applied to them in which case the references above to voltages should be regarded as references to currents.

As noted above, each train of biphasic rectangular pulses is timed to start at the end of the T-phase of the ECG, i.e. at points 56 in the diagram of FIG. 2C which shows an enlarged section of an ECG trace with the impulse trains 44 superimposed on it. In one specific example, the pulse repetition frequency of the biphasic rectangular pulses of each train is selected so that ten such pulses occur within the train duration. The train duration is usually selected to correspond to a time equivalent to from 10 to 25% of the TQ diastole duration of a human being undergoing treatment.

A typical value of the train duration will amount to 10% of the total duration of the heart beat, i.e. the R-R distance. Thus, the pulse repetition frequency delivered by the pulse generator 36 would, in this example, be ten pulses in one tenth of the duration of a heart beat, which might typically be equivalent to 1 second, thus resulting in a pulse repetition frequency of the individual pulses of the trains of 100 Hz.

For the purpose of giving a reasonable example, the amplitude of the output signal of the pulse generator 36, i.e. as applied to the electrodes 40, can vary from a positive amplitude 50 of plus 20 V to a negative amplitude 52 of minus 20 V.

It must be stressed that these values are simply given by way of example and that substantial variations may be made, depending on a whole variety of factors.

So far as the amplitude of the biphasic signal is concerned, it has been found that different patients have different threshold voltages at which they perceive the treatment as being uncomfortable. Thus, one possibility is for the operator 46 to vary the amplitude of the biphasic pulses until the patient perceives them as being slightly uncomfortable and then to reduce the amplitude slightly so that the patient suffers no discomfort.

Generally speaking, an amplitude with a lower limit starting from slightly above zero volts (say two or three volts) is possible. The upper limit has not yet been investigated, but depends, certainly, on whether the patient feels comfortable with the voltage level applied and the resulting current (very high voltages could be used in theory at least, providing the current is restricted to non-damaging values).

The relationship between the pulse width and the pulse interval of each train of pulses determines the total energy input into the muscles stimulated via the electrodes 40, 42. While a ratio of 1:10 has been found effective, this ratio can be varied substantially and indeed an interval is not absolutely essential. Generally speaking, with all patients a threshold is reached, depending on the pulse amplitude and the ratio of the pulse width to the interval, at which involuntary contractions of the muscle are apparent to a trained observer and the apparatus will usually be operated with amplitudes and ratios of the pulse width to pulse interval at levels at which apparent involuntary muscular contractions do occur, i.e. above the threshold value.

A particularly important reason for using biphasic pulses is to avoid the onset of electrolysis in the tissue affected by the applied impulses. Any effects of this kind which may be triggered during one half pulse are immediately reversed in the next half pulse. Although biphasic rectangular pulses of the kind described above have been found to be satisfactory and currently represent the preferred type of pulses, they are by no means the only possibility. Generally speaking, it is anticipated that the pulses delivered by the pulse generator will be biphasic in the sense that they have some positive going signal component and some negative going signal component. However, it is not out of the question that single phase rectangular pulses can also be used with advantage in some circumstances. It is certainly not essential that the negative half wave is of the same size and shape as the positive half wave. The positive half wave could be of different amplitude and width from the amplitude and width of the negative half wave. Moreover, it is not essential for the pulses to be rectangular pulses. They could be sinusoidal or they could have some other shape if desired.

As is apparent from FIG. 4, a preferred embodiment of the invention provides the operator 46 with seven different parameters which he can set during the treatment of a patient. The first of these is the delay or impulse delay, which, as shown in FIG. 2C, is the time difference between the Q wave end of a QRS heart signal and the effective start of the impulses, i.e. the start of the train or burst of impulses which commences at the end of the T-wave. The operator 46 has the possibility of adjusting this delay at 48, for example, by varying a potentiometer which determines the delay. This is an extremely important adjustment in the apparatus of FIGS. 2A and 4 for the following reason:

As will be explained shortly, the effect of the pulses is to unload the heart. This manifests itself by a reduction of the pulse rate, i.e. of the frequency of the heart beat. This means that the time between successive R peaks of the ECG trace increases. Not only does R-R increase, but the distance from Q to the end of the T wave also increases because it stands in a known relationship to the time interval R-R. Thus, if the delay were fixed, the start of the train of pulses 44 would not always coincide with the end of the T-wave due to the change in the pulse rate. Accordingly, with the apparatus of FIG. 2A, where the operator 46 forms an important link in the chain, the operator is able to adjust the delay at 48 to ensure that the train of pulses is always initiated at the end of the T-wave. By way of example, it is entirely usual when using the apparatus of the present invention, for the patient's pulse rate to drop from, say, 72 to 62 over a ten minute period, so that the operator 46 has plenty of time to effect the necessary adjustment.

It is believed that the best results are obtained when the delay is timed so that the train of pulses is initiated at the end of the T-wave. However, it is quite likely that beneficial results will also be obtained if the train of pulses starts slightly later than the T-wave and indeed the invention may still function if the train of pulses is initiated just before the end of the T-wave.

Practically speaking, it is considered desirable to keep the start of the train of pulses within a window between 5% of the length of the R-R path before the end of the T-wave of an electrocardiogram and 45% of the length of the R-R path after the end of the T-wave. In practice, with a particular patient, this delay can also be varied to see precisely which delay produces the most beneficial results with the patient.

Another parameter which can be varied by the operator 46 is the duration of the train of pulses applied to the patient after the end of each T-wave. As shown in FIG. 2C, the duration of a train is defined as the time between the start and the end of the impulses within a train or burst of impulses. This possibility of variation is indicated in FIG. 4 by the reference numeral 58.

The train itself is the package of electric impulses which are repeated one after the other for the time defined by the duration of the train. The number of electric impulses in each train can be varied by varying the output frequency of the pulse generator, i.e. the pulse repetition frequency of the pulses in each train of pulses, i.e. the number of pulses that are repeated per second if the train of pulses were to be one second long. Furthermore, the duration of the train determines how long the stimulation with a given frequency is repeated, i.e. how many impulses are effectively delivered within one heart cycle. This frequency and the duration of the train can be varied by the operator 46 at the input 60 in the example of FIG. 2A and FIG. 4. The other variable which can be readily changed by the operator 46 in the embodiment of FIGS. 2A and 4 is the amplitude of the biphasic rectangular impulses, i.e. the maximum difference between the peak value of the positive half cycle 50 and the peak value of the negative half cycle 52, as shown in FIG. 2B. This possibility of adjustment is indicated at 62 in FIG. 4. The amplitude is normally measured as a potential difference in volts. In an alternative embodiment (not shown) it is possible to plot a current curve rather than a voltage and to vary the amplitude with reference to the corresponding peak amplitude of the current curve.

In the apparatus of FIGS. 2A and 4 there are three further parameters of the pulses which are fixed, i.e. cannot in this embodiment be varied by the operator 46. The first of these parameters is pulse width, i.e. the time before the start and end of an electric impulse, as shown in FIG. 2B. The pulse width is selected in the example of FIGS. 2A and 4, so that the interval at a pulse repetition frequency of 100 Hz is ten times as long as the pulse width. That is to say by fixing the pulse width the interval will automatically vary as the pulse repetition frequency is varied. If the pulse width is made variable, as it is in some other embodiments, then varying the pulse width automatically results in the interval shown in FIG. 2B varying, on the assumption that the repetition frequency of the pulses of the train of pulses does not change. Box 64 in FIG. 4 relates to the input at which the fixed value of the pulse width is selected.

The further boxes 66, 68 in FIG. 4 represent two further parameters of the output of the pulse generator, which in the apparatus of FIG. 2A and FIG. 4 are fixed and not readily variable by the operator 46. Box 66 relates to the impulse form, i.e. the geometric form of the electric impulse resulting when the amplitude of the electric impulse is displayed over the entire impulse width. In the present example this is a biphasic rectangular pulse but it could have different shapes, for example sinusoidal or saw-toothed.

Box 68 refers to the possibility of changing the impulse mode which relates to the alternating mode of how impulse forms are repeated between electric positive and electric negative phase of impulses. In the present example the impulse mode is clearly biphasic, with positive and negative, but otherwise identical electric impulses alternating one after the other. This mode switch would, however, allow the operator to select some other mode, for example two positive half pulses followed by one negative half pulse.

One other aspect of the invention should also be mentioned with reference to FIG. 2A. This is the possibility of using a plurality of electrodes 40, 42. As mentioned above, the electrode 42 is a neutral electrode and it is only necessary to provide one such neutral electrode. However, more than one neutral electrode can be used when different areas of the body are treated, in order to allow a neutral electrode to be in the vicinity of each active electrode or each group of active electrodes. For long term treatment of a patient, it is however recommended to provide a plurality of active electrodes 40.

The reason is that the human body can become accustomed to the applied pulses and if only one active electrode 40 is provided, i.e. only one electrode to which the biphasic rectangular impulse signal of FIG. 2B is applied, the muscles that are stimulated by the potential between this electrode and the neutral electrode 42 gradually become tired and are stimulated less effectively. By applying the stimulating impulses to the different active electrodes 40 in sequence, it is possible to ensure that the muscle groups affected by the applied impulses do not become tired. The minimum number of active electrodes for sequencing is two.

Experiments have shown that by applying the output signal of a pulse generator to several electrodes 40 in sequence the treatment can be carried out over a period of many days without problem, and indeed only two electrodes are sufficient for this. However, three or four electrodes are preferred.

It is also possible to use just a single active electrode and to carry out the treatment over many days, provided the duration of the period of muscle contraction is restricted.

In the experiments done to date the first train of pulses 44 has been applied to the first electrode 40, the next train of pulses has been applied to the second electrode, the next train to the third electrode and the next train to the fourth electrode and the next train to the first electrode and so on. However, a sequence of this kind is not essential. It could be perfectly feasible to feed several trains of pulses to one electrode and then to change to the next electrode etc. Random energization of the electrodes with successive pulse trains or groups of pulse trains would also be entirely feasible.

It should be emphasized that there is nothing critical in the placement of the individual electrodes 40 and 42. Although these are shown in the stomach region of the patient under treatment here, they could be virtually anywhere on the patient's body. It is a surprising aspect of the present invention that the stimulation of any part of the peripheral vascular system with even small amounts of excitation energy have been found to produce the beneficial effect of the invention.

A more detailed discussion of the types of electrostimulation possible will be given later in the description.

It will be noted that FIG. 4 also shows with a series of boxes how the stimulation input to the patient from the pulse generator affects the body. Box 70 indicates that the stimulation can be direct stimulation or neuromuscular stimulation which is more usual. As noted above, the stimulation aspect will be described later in more detail.

Box 72 shows that the stimulation can be applied either to skeletal muscles or to smooth muscles. The effect of applying the stimulation to skeletal or smooth muscles is in both cases to produce a pressure pulsation in a local blood vessel of the peripheral vascular system indicated by the box 74. This local pressure fluctuation propagates via the blood, essentially an incompressible liquid indicated by box 76, to the heart indicated by box 78. Provided the pulses are timed correctly and applied in accordance with the teaching of the present invention, then they have been found to have a significant effect in reducing the heart load, which itself has an effect on the body of the patient indicated by box 80. This effect is picked up by the electrodes 30 of the electrocardioscope.

As noted earlier, a signal corresponding to the pulse rate, for example the R-R signal, is then passed on to the pulse generator and triggers the generation of the biphasic rectangular pulses of the individual pulse trains. The ECG wave form 82 is shown on the display 34 of the electrocardioscope as is the output signal of the pulse generator, as shown by the lines 82 and 84 in FIG. 4. The operator 46 has the ability to vary the impulse delay to ensure that each train of pulses starts at the end of the T-wave of the electrocardiogram or at the position deemed optimal in a particular case.

The operator 46 is able to see, by observing the display 34, how the patient's heart rate drops in response to the treatment and is able to vary the impulse delay accordingly. Although the impulse delay is conceptually considered as measured from the end of the Q-wave, it can be measured from another datum if required. It is in fact simpler to measure the impulse delay from the R peaks because these are larger signals which also occur at clearly defined times.

FIG. 3 gives a graphic representation of the effect of the treatment with the method and apparatus of the invention. The topmost curve 86 shows several peaks of an ECG wave form and is divided basically into three sections A, B and C.

Section A shows a patient's cardiac rhythm in a normal situation, i.e. without stimulation. Section B shows the cardiac rhythm for the same patient at the start of stimulation and section C shows the cardiac rhythm during continued stimulation. This division into sections A, B, C also applies to the further curves 88 and 90. In curve 86 section B shows the first train of impulses 44 which starts after the end of the T-wave and lasts for about 15% of the T-Q path. This same wave form repeats in phase C and continues repeating until the stimulation is terminated. The effect of this stimulation is to produce a significant reduction in the patient's heart rate so that the length between successive R positions of the ECG lengthens in the course of time. It will be noted that the R-R pattern in section C is longer than in section A, by a length labeled "b" as shown in curve 90 in FIG. 3.

Curve 88 shows the modulation of the muscular power resulting from the trains of electrical impulses such as 44. In phase A of line 88, there is no stimulation and accordingly the line is a straight line. The first stimulation occurs in the section B and results in a stimulation of a muscle which affects the peripheral vascular system. It will be noted that the muscle contraction 3 starts at the start of the train of pulses 44 and tends to reach its maximum contraction at the end of the train of pulses and then relaxes over a time period slightly longer than the train duration. It will be noted that the train of pulses 44 contains a plurality of stimulating electrical impulses but results in a simple muscular contraction. This muscular contraction 3 produces a pressure pulsation in the patient's peripheral vascular system which propagates back to the patient's heart.

The result of this can be seen from the curve 90, which is in fact a composite curve showing the pressure in the aorta and the left ventricular pressure. The left ventricular pressure starts from a base line value 92 and increases smoothly into a rounded peak 94, which has a value above the base line value 92 from the start of the Q wave until just after the end of the T-wave. Superimposed on this curve is a curve 96 for the pressure in the aorta.

At the point 98 the valves 20, 22 in FIG. 1C open and the pressure in the left ventricle is communicated directly into the aorta so that the pressure in the aorta rises at the same rate and with the same value as the pressure in the left ventricle until the end of the T-wave is reached, i.e. until the point 100 in FIG. 3, where the valves 20, 22 close again and the pressure in the aorta gradually sinks as the blood in it moves through the arteries of the human body. At point 98' the valves 20, 22 open again and the cycle repeats.

The effect of the muscular contraction, indicated by 3 in the curve 88, is to modulate the pressure in the aorta by a pressure wave traveling back to the aorta, from the peripheral blood vessel pulsation induced by the muscle contraction, so that in phase B it is slightly higher—shown as a visible hump—in the region labeled 2 than the corresponding value in phase A of curve 96. However, after the end of the muscular contraction, the pressure in the aorta sinks to lower values than were present in the corresponding section of the pressure curve in phase A.

At the same time it will be noted that the peak 94" of the left ventricular pressure has also reduced relative to the peak value 94 in phase A. The reduction in labeled 4 in FIG. 3.

What this means in practice is that the hump 2 in the pressure in the aorta in diastole results in increased coronary circulation, i.e. more blood and more oxygen is being supplied to the heart muscles, resulting in more energy being made available to the heart. This causes the pulse rate to reduce so that the duration of each heart beat increases from the value a before stimulation by the amount b to the value a+b after prolonged stimulation. The typical measured reduction with various probates is about 10 pulses per minute in the rest mode, for example 70 down to 60, or up to 30 or more at a high pulse rate, for example from 140 to 110, because of an increase of the DPTI/TTI ratio (diastolic blood pressure time index/time tension index).

In addition, the reduction indicated by 4 from the peak value 94 in phase A to the peak value 94" in the phase C represents a fall in the systolic pressure in the left ventricle and thus reducing left ventricular wall tension.

Bearing in mind that the heart load is proportional to the pulse rate times the systolic pressure, the effect of the invention in lowering both pulse rate and systolic pressure leads to a significant reduction in heart load.

The pre-systolic blood pressure, i.e. the pressure at the points 98, 98', 98" in FIG. 3 seems to reduce by about −5 mm Hg for a probate with normal blood pressure of 120/60. Extremely beneficial is the fact that with patients with blood pressure which is too high the reduction is far more pronounced, although the reduction in the heart rate for such patients tends to be less than for normal patients.

It is also noted that the cardioresonance electrostimulation of the invention not only results in a lower systolic pressure but also a steeper pressure increase in the systole, which can also be seen from curve 90 in phase C of FIG. 3.

Generally speaking it can be said that DPTI increases by some +10 to 15% depending on probates resulting from the hump in the blood pressure increase in diastole, reduced heart pulse rate and corrected by the difference from reduced pre-systolic blood pressure, assuming probates with normal blood pressure.

TTI decreases by some 4 to 5%, resulting from lower pre-systolic blood pressure corrected by the steeper pressure increase in systole (as shown at 7 in FIG. 3).

The benefit of this is that the DPTI/TTI ratio consequently increases by some 15 to 20% depending on probates for those having normal blood pressure. Thus, the typical heart load reduction is some 10 to 25% or more depending on the probates and their physical condition, which results from lower heart pulse rate and reduced systolic blood pressure and lower presystolic pressure. Furthermore, myocardial contractivity is improved, coronary blood circulation increased and ischemia reduced.

Turning now to FIG. 5, a similar apparatus can be seen to that shown in FIG. 2A, but with various modifications. Because of the similarity to the apparatus of FIG. 2A, the same basic reference numerals will be used to identify the items of apparatus in FIG. 5 and in FIG. 6 as were used in connection with FIG. 2A and FIG. 4, but increased by 100 for the sake of clear differentiation. Only those items where a significant difference is present will be specifically described. All items not specifically described with reference to FIGS. 5 and 6 but shown in the drawing will be understood to have the same function and operation as the correspondingly numbered elements in FIGS. 2A and 4. The description given to these elements in FIGS. 2A and 4 will be understood to apply to FIGS. 5 and 6.

The general arrangement of the patient 124 on the bed 126 is the same as before. The first significant difference in the embodiment of FIGS. 5 and 6 is the fact that the pulse generator 136 has been incorporated into the housing of the electrocardioscope 128. Despite this modification the arrangements of the electrodes 140 and 142 is the same as before and these are fed by the pulse generator 136 in just the same way as described above in relation to FIGS. 2A and 4. Equally, the electrocardioscope 128 has three sensor electrodes 130 connected to the patient in the heart region.

It should be noted here that different electrocardioscopes have different numbers of electrodes, depending on the precise measurements that are required. For the purpose of the present invention a simple measurement is sufficient. The operator is again schematically indicated at 146.

Another significant difference in FIG. 5 is the additional provision of a blood pressure meter 131 which is connected to a blood pressure measuring cuff 133 via the usual lines 135 (only one shown). Thus, in addition to carrying out an ECG measurement, a measurement of the patient's blood pressure is also effected. The blood pressure meter 131 has a display 137 on which the patient's blood pressure can be displayed, either as a curve or simply as different values for the systolic and diastolic pressure.

Referring now to FIG. 6 it will be noted that the layout of the pulse generator 136 is essentially the same as for the pulse generator of the embodiment of FIGS. 2A and 4. The same seven values for the pulses output by the pulse generator can be set as in the embodiment of FIGS. 2A and 4. However, in this embodiment all of the parameters are variable and indeed either by the operator 146 or automatically. When the apparatus is intended for manual adjustment, the operator is able to effect the individual settings via respective inputs 148' to 168'. Alternatively, all these settings can be effected electronically via a suitable external program interface 141, which communicates with an input program interface 143 connected to the pulse generator, which is preferably realized as a chip. The communication between the external interface 141 and the internal interface 143 can be direct, i.e. by hard wiring, or can be indirect, for example by way of an infrared transmitter or the like.

When the settings are effected automatically, the pulse generator, i.e. the control unit controlling the operation of the pulse generator is programmed to either detect the end of each T-wave, or to calculate the time position of the end of each T-wave from the data provided by the electrocardioscope and to automatically control the triggering of the pulse train so that each train is automatically triggered at the end of each T-wave. Such synchronized operation of a pulse generator is well known generally in the electronic arts, for example in transmitters which respond to acknowledge an incoming signal, and can thus readily be realized by a person skilled in the art.

In addition, the apparatus shown in FIG. 6 is provided with a data storage system 151 including a memory which is able to store any desired parameters or measured values of the apparatus. Thus, the storage system can be designed to store, optionally in compressed form, full wave ECGs over a period of time, for example an hour, a day or a week, and also data relating to the patient's blood pressure in the same intervals. The external program interface can also be used to read out the data contained in the data storage system.

Another special feature of the apparatus of FIG. 6 is the safety cutout 161. The point of this safety cutout is to analyze the measured parameters and to compare them with established parameters so that the treatment can be automatically discontinued if the measured parameters show any undesirable deviation from the desired values.

By way of example, limiting values for critical parameters such as the pulse rate and the systolic or diastolic pressure can be registered and stored in the safety cutout, or in a memory associated with the apparatus to which the safety cutout has access. During electrostimulation the safety cutout receives values corresponding to the pulse rate and the systolic and diastolic blood pressure and checks whether any of these values are higher or lower than the limit values set before the start of electrostimulation. Should any of the values rise above the limit values, or rise above the limit values by a significant amount, then the safety cutout will be programmed to operate to alert the operator 146 and/or to shut off the pulse generator if appropriate. The limit values can also be set to be the initial values before electrostimulation.

The safety cutout could also be designed to trigger its function, for example to cutout stimulation or to signal an alarm, if statistical deviations of the input signal are detected over a certain time period or when heart arrythmia are detected.

Moreover, the safety cutout can also compare the patient's pulse rate and blood pressure values with stored lower threshold values, which are set at a safety level, below which they should not fall. Should the measured values during electrostimulation fall below the minimum safety values, then again the operator can be alerted and/or the system can be automatically shut down. Rather than using actual measured values taken from the patient himself to define the upper limits of the critical parameters, it is also possible to program the safety cutout, for example using the external and internal program interfaces 141 and 143 with appropriate values from a normal, healthy person or from a person suffering from the same typical problem as the patient undergoing treatment.

The apparatus of FIGS. 2A and 4 and FIGS. 5 and 6 are clearly used for the treatment of patients in a reclining state.

The invention is, however, quite capable of being used by patients going about their normal daily lives.

Thus, FIG. 7 shows a patient equipped with a suitable apparatus for carrying out the treatment throughout the course of a normal day while going about his normal daily life, or during sleep.

For the sake of consistency, items or apparatus in the present embodiment which correspond to those of the embodiment of FIG. 2A will be designated with the same general reference numerals but increased by 200. Again, the description previously given will be understood to apply to items not described in detail but having the same general reference numeral as used in FIG. 2A.

Thus, the apparatus of FIG. 7 comprises an elastic chest bandage which includes two heart pulse rate sensors 253 and a wireless transmission unit 255 for transmitting a signal corresponding to the heart pulse rate to a receiver 257 incorporated into an elastic waistband, for example of a pair of pants 267. The receiver 257 forms part of an electrostimulation unit comprising a pulse generator 236 with an inbuilt battery. The pulse generator 236 is again connected via wires to corresponding electrodes 240 and 242, of which only one active electrode 240 and one neutral electrode 242 are shown in FIG. 7. It will, however, be understood that a plurality of active electrodes 240 can be provided as aforesaid.

A heart pulse rate sensor with a radiotransmitter unit of the kind used here is available for use by athletes under the trade name "Polar" (registered trade mark). In the "Polar" transmitter two electrodes are provided to detect an electrical signal on the wearer's skin. The electrodes are mounted on a sealed transmitter that is attached to the patient's chest by way of the elastic chest bandage. The Polar transmitter detects the voltage differential on the skin during every heartbeat and sends the signal continuously and wirelessly using electromagnetic fields to a wrist receiver. The receiver is modified, not to be in a wrist watch, but instead built into a waistband, as aforesaid. The method used in the Polar transmitter is based on ultralow/power consumption, which is guaranteed with the unique insertion mode at electronic module and carefully designed and tested circuitry to pick up the electrical signal of the heart. The operation of the apparatus of FIG. 7 is basically the same as the operation of the apparatus of FIG. 4, as can be seen with reference to the block circuit diagram of FIG. 8.

The similarity to the apparatus of FIGS. 2A and 4 and to the apparatus of FIGS. 5 and 6 can readily be seen from FIG. 8. It will be noted that a display 263 is provided which can take the form of a small liquid crystal display mounted, for example, on the waistband of the pants. The display 263 would normally display just the patient's pulse rate, but could optionally display any other desired information, for example the settings of the pulse generator. Here the settings of the pulse generator can be controlled by the patient himself 224 or by an operator 246 if the apparatus is fitted to a patient in a surgery, for example. The patient 224 or the operator 246 can control the seven variable settings—or only some of them if the others are fixed—via corresponding manual inputs 248', 258', 260', 262', 264', 266' and 268', which could, for example, be realized as keys on a small keyboard. Alternatively, a program interface 243 can be provided which can be used to program the pulse generator by a separate input program program interface 243, as in the apparatus of FIG. 6.

As noted above, the apparatus of the present invention is provided with a simple pulse rate meter in order to deliver an R-R signal which is quite sufficient to control the pulse generator 236 to provide the correct stimulating pulses at the correct time. It is not necessary to actually measure the end of the T-wave to control the delay of the pulses, because the QT path is known to have a well-defined relationship with the R-R path and thus the end of the T-wave can easily be calculated from the signals generated by the pulse rate meter.

It will be noted that it is not essential for the signals from the pulse meter to be transmitted by radio to the pulse generator 236. The signal could easily be transmitted using small wires if desired. Moreover, there are numerous pulse rate measuring sensors instruments available which are very small and unobtrusive and can be used at a location other than immediately in the vicinity of the patient's heart. Any of these known pulse rate measuring sensors can be used for the purposes of the present teaching. In the embodiment of FIGS. 7 and 8 there is also a safety cutout 261, but here the safety cutout only responds to the patient's heart rate, i.e. only operates to signal alarm and/or switch off the pulse generator if the patient's pulse rate goes too high or too low or when statistical deviations occur over a certain period of time or when arrythmia is detected. It would also be entirely feasible to incorporate a portable ECG apparatus into the apparatus of FIGS. 7 and 8 and to equip the apparatus with a data storage system as shown in FIG. 6 so that a long term ECG can be measured in conjunction with the apparatus of the present invention.

A possible modification of the apparatus of FIG. 7 is shown in FIG. 9. Here the same basic reference numerals are used as in the apparatus of FIG. 8, but prefixed with the number 300 rather than 200. It will be seen from a comparison of FIGS. 8 to 9 that the only real difference is the addition of a blood pressure meter 365 which can also pick up a suitable signal from a patient's body and enable this signal to be shown on the display 363. In addition, if a blood pressure meter is provided, it can also be connected to the pulse generator as a variable input signal in parallel to the pulse rate R-R. For cases in which the heart rate signal is switched off, the output signal of the blood pressure meter can be the only input signal to the pulse generator, so that the apparatus is also able to operate without a separate pulse rate measurement. Moreover, the blood pressure meter can also be connected to the safety cutout 361, so that an alarm is given should the patient's blood pressure rise or fall beyond safe limits.

The controller of the pulse generator can use either one of the single input signals as the control parameter. I.e. the controller can use either the heart pulse rate signal 238, see e.g. FIG. 8, or the systolic blood pressure signal included in signal 365, as the control parameter. Alternatively the controller of the pulse generator can use a combination of the two input signals, i.e. the heart pulse rate signal 238 and the systolic blood pressure signal in 365 in parallel, see e.g. FIG. 9.

If the controller uses as the control parameter a factor resulting from the heart pulse rate signal multiplied by a factor relating to the systolic blood pressure—then the multiplied factor is proportional to the heart loading. The first measurement of the input signal or signals entering the controller when it is started, i.e. the value of the input signal or signals before the start of the stimulation will determine the factors with the value of 1. Every deviation of the factors will be measured by the controller relative to these starting values having the value of 1, when comparing the effective result achieved versus the intended reduction of the multiplied factors, which is proportional to the reduction of the heart load being aimed for.

This means that when the two input signals are used in parallel, see e.g. FIG. 9, the controller aims to minimize the multiplied factors of the two input signals (heart pulse rate and systolic blood pressure—being proportional to the heart load directly) by varying one or more of the seven variable parameters of the pulse generator, numbered 248 to 268 in FIG. 9, according to algorithms which are programmed into the microchip forming the control unit of the pulse generator 236. If the two input signals, heart pulse rate and systolic blood pressure are not measured at the same intervals and/or not with the same timing relative to the QRS complex of the heart, the controller will always use the latest valid factor for each input signal for the multiplication.

If only one of the two input signals is being used—either the heart pulse rate, see FIG. 8, or the systolic blood pressure alone—then the not present input signal is given the constant value of 1 for the multiplication of the factors. In this case, the heart load is being regarded as proportional only to the selected input signal. This means that the controller aims to minimize the selected input signal—either the heart pulse rate or the systolic blood pressure—by varying one or more of the seven variable parameters of the pulse generator, numbered 248 to 268 in FIG. 8, according to algorithms which are programmed into the microchip.

In the case of a portable apparatus it would be advisable for the safety cutout to be provided with an alarm so that the patient is alerted to a dangerous condition and look at the display and switch off the pulse generator or stop whatever labor or exercise he is undertaking.

It should be noted that the portable apparatus of FIGS. 7, 8 and 9 is particularly suitable for all categories of treatment described in the introduction to the specification and in particular for lipolysis and body shaping treatment and helping athletes improve their performance, in training various muscle groups of the body and in general improvement of a person's condition and physique. If particular muscle groups are to be trained, for example muscles concerned with the urinary tract or the sphincter muscle, then special electrodes need to be placed accordingly, so that the required local stimulation takes place.

Further details relating to the electrostimulation of the body will be given with reference to the diagram of FIG. 10.

FIG. 10 is a schematic diagram illustrating how the method and apparatus of the present invention works on the human body.

FIG. 10 is basically a combination of elements of the diagram of FIG. 4 with elements of the diagrams of FIG. 1. Accordingly, the same reference numerals will be used.

FIG. 10 shows that electrostimulation is applied directly or as neuromuscular stimulation 70 to either skeletal or smooth muscles that are indicated by box 72. These muscles act on the peripheral vascular system of the patient to cause peripheral blood vessel pulsation indicated by box 74. This is transmitted through the blood in the patient's body as a pressure waveback to the aorta AO, where a corresponding pressure increase arises. The pressure pulsations affect the circulation of the blood in the patient's body indicated by 70 and in particular increase the coronary circulation through the coronary arteries CA. These directly oxygenate the heart 10, which in turn affects and improves the pumping of blood through the patient's body. Thus, the better pumping of the heart 10 results in an affect on the aorta, hence the double arrows between the box AO for the aorta and the box 70 for the patient's blood system.

The improved blood flow through the aorta also has an effect on the peripheral vascular system, since the blood flow there is improved as well. Clearly improved blood flow into the peripheral vascular system results in increased blood flow back through the veins 71 to the heart, as indicated by the arrow 12 in FIGS. 1B and 10.

FIG. 11 now explains various different concepts of neuromuscular electrostimulation. More specifically, FIG. 11 shows a bundle of nerves 400 which pass to muscle fibers 402 of a skeletal muscle 404.

As before, for example in the embodiment of FIGS. 2A and 4, the neutral electrode is labeled 42. FIG. 11 shows two different active electrodes 40 and 40'. The active electrode 40 is positioned close to a location where the bundle of nerves 400 is fairly close to the surface of the skin. In this case the active electrode 40 stimulates the bundle of nerves 400. By stimulating the bundle of nerves 400 it stimulates the muscle fibers 402 in the muscle 404, to which the bundle of nerves 400 leads. This is a typical example of neuromuscular electrostimulation.

In contrast, the active electrode 40' is not positioned close to a bundle of nerves 400, but rather in the immediate proximity to the muscle 404, so that it stimulates the muscle fibers 402 in the muscle 404 directly. This is called direct stimulation. Generally speaking, direct stimulation requires more power and higher voltages or currents than neuromuscular stimulation. Direct stimulation is, however, particularly important in the rehabilitation of patients such as paraplegics, where a bundle of nerves, such as 400, may have been cut for some reason or other, for example due to an accident.

In some cases a bundle of nerves such as 400 passes very close to the surface of the skin, for example in the back, close to the spine, so that a type of nerve stimulation is possible referred to as transcutaneous electrical nerve stimulation (TENS), this being a special case of neuromuscular stimulation.

All the electrostimulation discussed to date has taken the form of electrostimulation and indeed it will be noted that the pulse generator apparatus shown in all the variants described hitherto has a closely similar layout, irrespective of whether it is used for the stationary treatment of patients in hospitals or clinics, or for outpatient treatment in some form or another. This is a particular advantage of the invention. It means that a dedicated chip can be made for the pulse generator and the associated electronic functions and control devices and elements. The same basic module can be used for all different types of equipment, thus enabling mass production and cost and space savings. Through the ability to incorporate all the required functions on a single chip or on a plurality of small interconnected chips, there is very little weight for a patient to carry around, and indeed, as will be discussed later, the equipment can be incorporated into an existing cardiostimulator, or implanted into the human body for long term use.

Electrical stimulation is, however, not the only way of using the present invention. A number of other ways of using the invention will now be described with reference to FIG. 12.

Where items are used in these diverse embodiments which correspond to the items of equipment in any of the previously discussed embodiments, then the same reference numerals will be used to facilitate as understanding of the invention. It will be understood that where reference numerals are used in FIG. 12 which have counterparts in earlier Figures, then the description given to those counterparts also applies here.

FIG. 12 shows a patient 124 sitting on a chair 125, with the patient having three electrodes 30 forming the ECG measuring set and connected to a combined pulse generator 136 and electrocardioscope 128 with a display 134. In addition, the pulse generator and electrocardioscope 136, 128 includes a blood pressure meter 131 connected by the usual lines 135 to a blood pressure measuring sleeve 133, which could be realized differently in accordance with any known blood pressure measuring instrument.

On the patient's leg there is a bandage 500 incorporating a pressure pad 502, which is connected to a generator 504 for generating fluid pulsations using any gas or liquid. For this purpose the fluid pulsation generator 504 is connected to a pressure source 506 and is connected via a line 508 to the pressure pad. Included in the generator for fluid pulsations is an inlet valve and an outlet valve (not shown), which are controlled via signals delivered from the pulse generator 128 combined with the electrocardioscope 136. That is to say, the electrical pulses delivered by the pulse generator 128, which can for example have the triangular sinusoidal or rectangular wave shape shown in FIG. 12A are used to initiate the opening and closing of valves in the fluid pulsation generator, so that when the inlet valve is open and the outlet valve is closed, a pressure pulse is applied to the pressure pad 502 via the line 508, and so that when the outlet valve is opened and the inlet valve is closed, the pressure pad 502 is vented through the outlet valve. Accordingly, pressure pulsations are applied to the patient's leg in accordance with the selected wave form.

Generally speaking, only one pulse will be applied for each beat of the patient's heart, and again the pulse will be applied directly after the end of the T-wave so that the stimulation takes place in counterpulsation. Again, the pulse generator 128 incorporated in the electrocardioscope 136 is designed so that it automatically follows the changing position of the end of the T-wave which is dependent on the patient's pulse rate. The blood pressure measurement can again be used for checking purposes and/or as an input signal to the pulse generator or to trigger a safety device. Input signal combinations could be used, for example as schematically shown by the switches between box 180 and the boxes 514 and 516.

FIG. 12B illustrates how the apparatus of FIG. 12A operates. Again it can be seen that the fluid pulsation generated by the fluid pulsation generator 504, as triggered by the pulse generator 128, applies pressure pulsations to the pressure pad 502, which results in compression of the patient's tissue 508 in the vicinity of the pressure pad and thus to compression of the patient's muscle, as shown by box 510. The compression of the tissue and of the muscle results in corresponding pulsation of a blood vessel in the peripheral vascular system, as shown by box 512. This pressure pulsation is transmitted via the patient's blood 176 to the patient's heart 178, where it affects the patient's heart pulse rate. The affect on the heart 10 causes the heart to have an affect on the patient's vascular system, i.e. on his body indicated schematically at 180. More specifically, it affects the patient's pulse rate at the sensing location, as indicated by box 514, and the patient's blood pressure, as indicated by box 516. The heart pulse rate is passed on to the pulse generator to ensure that the pulse is generated or timed correctly with respect to the end of the T-wave. The blood pressure is also shown connected to the pulse generator.

The embodiment of FIG. 12 could be executed using a portable pulse generator in a similar way to the embodiment of FIG. 7. I.e. similar small equipment and possibly radio transmission for the signals from the sensor electrode(s) can be used in place of the stationary equipment shown in the sketches.

FIGS. 13 and 14 show that the present invention can also be used with a known cardiostimulator, for example in the form of a pacemaker or defibrillator.

In order to understand FIGS. 13A and 14, it is helpful to consider the function of a pacemaker with respect to FIG. 13B and the function of a defibrillator with respect to FIG. 13C.

FIG. 13B shows the typical ECG trace of a patient fitted with a pacemaker. The typical pacemaker patient has an irregular heart beat, which for example means that the heart misses a beat every so often. In a modern type of pacemaker, the pacemaker senses a missing heart beat and immediately triggers a stimulation signal such as 612 which causes the heart to beat just a fraction later than it would have done had the heart beat occurred at the correct time. It can be seen from this that the pacemaker effectively measures an electrocardiogram and in any event contains all the information on the repetition frequency of the R peaks necessary to trigger a pulse generator to apply stimulating signals in the counterpulsation mode in accordance with the invention. Thus, FIG. 13B shows such trains of stimulating impulses 44 at the end of the T-wave. The stimulating pulses are applied as shown in FIG. 13A to a muscle close to the patient's heart, since, in accordance with the invention, it does not matter which muscles of the peripheral vascular system are chosen to provide pressure pulsations in the peripheral vascular system which affect the heart.

FIG. 13C shows the situation with a patient suffering from fibrillation. For the trace shown in FIG. 13C, the first two heart beats are normal, but then the regular electrical wave, which regulates the heart beat, goes into fibrillation, i.e. the patients heart stops beating regularly and the electrical wave fluctuates wildly. A defibrillator follows the ECG trace and recognized when a heart beat is missed and fibrillation occurs. To get the heart beating normally again, the defibrillator applies a significantly higher electrical signal 614 to the heart than is usual and it can be seen that the heart starts to beat again normally following defibrillation.

Thus, a defibrillator, which is another form of cardiostimulator, also follows the ECG trace of the patient to which it is fitted and thus has available all the information on the repetition frequency of the R-R peaks which is necessary for calculating the end of the T-wave and applying stimulating pulses to the patient's peripheral vascular system in accordance with the present invention. Accordingly, it is possible to take a standard cardiostimulator, for example a pacemaker or a defibrillator, and to add to it circuitry, for example in accordance with FIG. 8, to enable stimulating pulses to be applied to the patient's peripheral vascular system.

FIG. 13A shows such a combination. Here the patient's heart 178 is schematically illustrated and the cardiostimulator is indicated by reference numeral 620. The arrow 622 represents the pacemaker following the electrical signals of the heart and the arrow 624 represents the trigger pulse sent back to the heart by the pacemaker 620 when a missing beat is sensed.

As mentioned above the pacemaker 620 has been supplemented with the circuitry of FIG. 8 in a miniaturized form and also has output leads 626 which lead to respective electrodes 640 and 642 provided on a muscle 628 which may be close to the heart, so that the leads do not have to extend over a substantial distance to the patient's body. Thus, the modified cardiostimulator 620 of FIG. 13A can find the timing of the R-R-peaks from the ECG trace, can calculate the end of the T-wave using the known relationship between the Q-T and R-R pulse and can time stimulating pulses 44, so that they are initiated at the end of the T-wave to obtain the beneficial effects of the present invention. Precisely the same situation applies to the case of a defibrillator, in this case the cardiostimulator 620 in a combination of a defibrillator with the apparatus of the for example FIG. 8 of the present invention. Because the apparatus of FIG. 13A will be used for long term treatment, it is reasonable to use a plurality of active electrodes 640 (at least two) for the reasons given above. This also applies to the embodiment of FIG. 14.

FIG. 14 illustrates another way of realizing the present invention in combination with a cardiostimulator 620 which again can, for example, be a pacemaker or a defibrillator. In this case the cardiostimulator 620 is supplemented by a radio transmitter 630 and this transmitter 630 transmits radio waves through the patient's body containing information on the R-R peaks or the end of the T-wave to a further apparatus 632 which is constructed in accordance with the invention, for example in accordance with FIG. 8, and is located at a different position in or on the patient's body. In this case, the apparatus 632 would include its own battery and again will transmit the required stimulating pulses to electrodes 640 and 642 affecting a muscle 628 which again produces pulses in the patient's peripheral vascular system. It will be noted that the battery required for an apparatus such as 632 can readily be of the same size and type as that used for a pacemaker. Since the apparatus of the invention, for example in accordance with FIG. 8, can easily be miniaturized using modern semiconductor chip technology, the whole implanted apparatus 632 certainly need be no larger than a typical cardiostimulator and can indeed be smaller. In the embodiment of FIG. 14 the apparatus 632 and the associated electrodes can either be implanted in the patient's body or provided externally thereof.

Turning now to FIG. 15 there is shown another way of realizing the present invention in combination with a cardiostimulator 750, which is here realized as a cardiomyostimulator modified to additionally satisfy the present invention. As explained above, the cardiomyostimulator 750 comprises a cardiac pacemaker 720, which communicates with the heart 178 so that it receives electrical signals of the heart 178, as symbolized by the arrow 722, and sends trigger pulses back to the heart 178, as symbolized by the arrow 724. In addition, the cardiomyostimulator 750 includes, as known per se, a programmable divider 752 which operates to send a burst of electrical pulses beginning typically at the end of the R-wave and ending typically at the end of the T-wave to a muscle 754 wrapped around the heart via leads schematically illustrated by the line 756.

As already explained above in connection with the prior art, this muscle 754, which has to be implanted by a surgical technique, is stimulated in the simpulsation mode.

In accordance with the present invention, the programmable divider 752 is, however, programmed to trigger a further train of impulses which begins exactly at the end of the T-wave and to send these trains of pulses via leads 726 to any desired skeletal or smooth muscle 728, other than a heart muscle, so that this muscle is stimulated to contract in the counterpulsation mode, thus affecting the patient's peripheral vascular system and causing cardioresonance in accordance with the invention.

Thus, in this version of the invention, the cardiac pacemaker 720 consists of a sensing amplifier which monitors the intrinsic heart rate as symbolized by the arrow 722 and has an output stage which paces the heart, as symbolized by the arrow 724, as soon as the heart rate drops below a programmed value. Thus, a cardiac event can be sensed or initiated by the device as in a synchronized pacemaker.

Furthermore, the cardiac pacemaker 720 triggers a synchronization circuit (not shown but known per se). The trigger signals are processed through programmable divider which allows for different heart/wrapped around muscle contraction ratios within the heart muscle conglomerate (178+754). A delay is then initiated after which the myostimulator is enabled, sending a burst of pulses via leads 756 to the wrapped around muscle 754. In accordance with the present teaching the programmable divider of the synchronization circuit 752 then also produces a train of pulses which are applied to electrodes provided at the muscle 728.

The relationship between the pulses applied in the simpulsation mode to the wrapped around muscle 754 and the pulses which are applied to the muscle 728 in the counterpulsation mode can be seen from FIG. 16 in relationship to the ECG trace shown there. This drawing also indicates the synchronization pulse 712 associated with the pacemaker function.

FIG. 17 is closely similar to the arrangement of FIG. 15, but here the cardiomyosimulator 750 includes a wireless transmitter 730, which transmits wireless signals to the receiver 732 at or close to the muscle 728. There they are used to trigger stimulating pulses for application to the muscle 728, in similar manner to the embodiment of FIG. 14. In both cases, i.e. in the embodiments of FIGS. 14 and 17 the actual pulse generator is incorporated in the cardiostimulator and simply triggers stimulating pulses the power source incorporated in the receiver for application to the muscle 628 or 728 respectively. However, the respective receiver 632 or 732 could also be a part of or associated with a pulse generator located directly at the respective muscle 628 or 728, in which case the signals transmitted to the receiver are trigger signals for the pulse generator and indeed with or without the relevant delay.

In the arrangements of FIGS. 15 and 17, the simpulsation of the heart muscle conglomerate (178+754) assists the heart pumping function and is immediately followed by the counterpulsation of the peripheral muscle 728, which leads to increased coronary flow, oxygenation of the heart and a reduction in the heart loading.

One important development of the invention in relation to electrical stimulation lies in a special gating apparatus.

Heart rate sensing devices used on mammals (ECG traces, heart rate monitors etc.) measure the electrical heart signals at various points of the body using either skin electrodes for noninvasive measurements or implanted leads for invasive measurements. In both cases the electrical signal measured is relatively small and depends on the measurement location. For example, the electrical heart signal measured by noninvasive skin electrodes on the surface of the thorax of a human being is typically some 3–4 mV maximum amplitude for the R-peaks.

However, the electrical signals required for stimulating muscles are of much higher magnitude compared to measured heart signals. For example, the electrical signal used for creating a strong isometric muscle contraction on a skeletal muscle of a human being via neurostimulation has a magnitude of +/−20 V, and, for direct muscle stimulation, when neurotransmission is no longer possible, this required electrical signal might be much higher.

When using a heart synchronized electrical muscle stimulation, a very disturbing phenomena can be observed, which we call interference.

When using any measured heart QRS trace, for example as shown in FIG. 18, the trigger signal is usually derived from the positive rising slope of every R-peak. The trigger signal is generally a digital trigger signal, such as 1 in FIG. 18. This trigger signal initiates the electrical muscle stimulation signal after the required delay, at a time within the delay window described earlier. Since this stimulation signal is an electrical signal with a magnitude many times higher than the heart rate signal itself, the electrical stimulation impulse is transmitted on the human body and consequently the heart signal sensor also senses the electrical stimulation signal. If now the control setting is such that the stimulation pulse for the muscle is delivered in counter-pulsation to the heart, as can be seen from the pulses of train 1 in FIG. 18, the trigger unit now receives from the heart rate sensor not only the wanted trigger input to trigger the trigger signal 1 of the R-peak, but also within the R-R cycle, exactly at the moment of the muscle stimulation (controlled by pulse train 1 which is delivered after the delay relative to the R-trigger signal), the much higher electrical signal delivered to the muscle, which is marked by interference in FIG. 18, and now this now triggers trigger signal 2. This trigger signal 2 now leads to a second, unwanted muscle stimulation marked by the pulse train 2 in FIG. 18 within the same R-R cycle at exactly the same set delay, however now after trigger signal 2. This second unwanted stimulation from pulse train 2 is perceived by the stimulated person as a sudden surprising disturbance which is completely irregular in comparison to the calming rhythm expected from the counterpulsation mode. As a result, the heart rate immediately increases sharply, probably via neurotransmission to the brain and to the heart. Synchronized stimulation in counterpulsation does not work when such interference is present, and the wanted heart load reduction cannot then be achieved.

The present invention provides a means of avoiding such an unwanted electrical interference of the sensing and stimulation signals by a gating mechanism which effectively closes an interference window, see FIG. 18, after the trigger signal 1 from the heart rate sensor has been registered by the control unit. This interference window is reopened by the control unit in time to accept the wanted trigger pulse 1, but is closed to avoid the unwanted trigger pulse 2.

By way of example, a practicable execution of this gating mechanism is realized in the form of software controlling a microprocessor, whereby the rising edge of the digital trigger signal 1 triggers the microprocessor into an interrupt routine and then the closing of the interference window is activated by a software gate which disables the acceptance of any unwanted trigger signal, for instance trigger signal 2, from being transmitted to the microprocessor, as long as the interference window is closed. Closing and opening of the interference window is set by programmable, adjustable setting values which are selected relative to the measured R-R cycle.

This adjustable timing for closing and reopening the said interference window permits the reliable functioning of this interference window to be optimized, depending on the heart QRS trace sensing device being used, and taking account of the reduction of heart frequency resulting from heart unloading.

One important way of optimizing the timing of the stimulation signals applied to the patient will now be described with reference to FIG. 19. This optimization scheme can be applied to any type of stimulation, i.e. not just to electrical stimulation.

Here a programmable algorithm defines the way an adaptive control unit automatically finds the lowest possible heart load. First of all, realistic minimum and maximum values for the delay are defined, i.e. for the delay from each R-peak to the triggering of the stimulation signal. These limits are shown in FIG. 19 and are set relative to the prevailing heart rate as measured from successive R-R peaks. The minimum delay will usually be selected at or just before the start of the delay window, i.e. at or just before a time corresponding to 5% of the R-R path before the expected end of the T-wave, for example as calculated using the so-called BAZETT-relationship. As a safety precaution, a maximum delay is selected, which should occur just before the P-wave. The maximum delay could, however, be omitted.

An offset value is now defined and is added to the minimum delay and used to define the time at which stimulation signals start. A typical initial value for the offset could be 5% to 10% of the R-R path. Stimulation is now commenced using this time delay, i.e. minimum delay plus offset, and the heart rate is monitored by measuring the distance between successive R-R peaks. If a reduction of the heart rate, i.e. a lengthening of the R-R path, occurs, then a reduction in the offset is effected by a predetermined amount, for example a fixed fraction of the original offset, and a check is again made as to whether the heart rate has reduced. If so, the offset is again reduced and this iterative process is continued until no further reduction in the heart rate is detected, or alternatively until the minimum heart rate set in the safety cutout has been reached, or until the heart rate increases again.

A renewed increase in the heart rate indicates that the delay (minimum delay plus offset) is no longer at an optimum value.

If the heart rate increases, then the offset should also be increased in an attempt to reduce the heart rate. Once the heart rate starts to increase again, then this is an indication that the offset is now too large. This signifies that the optimal value of the offset has been found, namely the value of the offset which resulted in the minimum heart rate. The offset can now be returned to this optimum value.

A similar procedure could be adopted for the duration of the stimulation applied or to any other relevant parameters. The process described above can also be carried out having regard not just to the heart rate, but also to the systolic blood pressure, i.e. to the value of the rate heart multiplied by the systolic pressure, which defines the heart load. This measurement can, and generally will, be made over a number of heart cycles.

With the alternative of stopping after optimization, the adaptive control system according to the programmable algorithm can optionally repeat this iterative optimization procedure steps in regular, defined and adjustable time intervals.

These time intervals can be adjusted individually for one or more different time windows, i.e. elapsed time periods, calculated from the start of treatment.

There are different ways of how the end of the T-wave of a heart QRS trace can be derived. One of them is by calculating the Q-T value based on known and published statistical average values relative to the Q value, which is close to the trigger timing of the trigger signal triggered in heart rate sensors (ECG or QRS trace of heart rate monitors etc.) on the positive slope of an R-peak. Another method would be to detect directly the end of the T-wave.

Because individual persons are different from each other, a calculated Q-T value based on statistical averages would have to include sufficiently high safety margins for the delay in order to avoid unwanted pulse trains being delivered constantly during the T-wave. Practical tests carried out using the invention have shown that the maximum heart load reduction can be achieved when stimulation starts end of the T-wave. It has been concluded that it is advisable to use an adaptive control system which starts stimulation with a delay, which includes sufficient safety margins based on the statistical average, however then automatically finds the individual best optimum delay which results in a maximum possible heart load reduction. This has a significant commercial importance, because with such a self adaptive system, all units can be manufactured in exactly the same way, but the adaptive control system will adapt itself to the individual needs of each person. The present invention allows such an adaptive control.

For example, a practical realization of such an adaptive control system is referred to in FIG. 19. The heart rate is sensed with, for example, an ECG cardioscope, which inherently triggers a trigger signal at the positive slope of an R-peak. Any other form of heart rate sensor, such as a heart rate monitor, can be used which similarly triggers a trigger signal at the positive slope of an R-peak. This trigger signal controls the control unit as the input signal, the control unit for example being a programmable microprocessor.

Minimum delay is calculated based on known statistical Q-T values and set with an adjustable factor. One practical example of such a calculation is the published so called Bazett formula which allows to calculate the Q-T value proportional to a factor k (different for men and women) multiplied with the square root of the R-R heart rate cycle time. With this, a minimum delay relative to the R-R cycle can be set. An adjustable offset value can be set. This means that the start of pulse trains will be set at the minimum delay plus the set offset value. Optionally a maximum delay can be set.

The microprocessor automatically executes the iterative steps as described above by means of the built in programmable algorithm to find the minimum heart load within the set minimum delay, safety window and time.

The previous description has also included embodiments in which stimulators in accordance with the present invention are combined with various types of cardiostimulator. It will be appreciated that these combinations can be further adapted to incorporate the features of the embodiments of FIGS. 18 and 19.

It should be noted that the arrangement of FIGS. 2A, 4, 5, 6 and 9 is currently the best known mode of performing the invention on an inpatient.

The embodiment of FIG. 8 currently represents the best known mode of performing the invention on an outpatient. The data storage option is only used when the patient is being treated by a therapist or a skilled person, i.e. for a cardiovascular disorder. For the training of athletes or for body shaping it is considered unnecessary.

The embodiment of FIG. 14 is currently considered the best known mode of treating a patient with a heart disorder requiring a pacemaker or a defibrillator.

What is claimed is:

1. Apparatus for treating a mammal or other living organism having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said organism having a pulse rate and a systolic pressure resulting from the action of the heart, the apparatus comprising means for measuring the heart rhythm, means for producing pressure pulsations in the peripheral vascular system by a non-invasive or invasive method in synchronization with the heart rhythm in the counterpulsation mode, determining, for each periodically repeating heart rhythm, a time corresponding to an end of each T-wave, means for varying at least one parameter of such pressure pulsations to produce an optimized reduction in at least one of said pulse rate and said systolic pressure and thereby a net reduction in said heart load, means for initiating the pressure pulsations in the peripheral vascular system by stimulation signals triggered in a time window lying within a range of 5% of the R-R path length before the end of the T-wave and 45% of the R-R path length after the end of the T-wave and means for selecting the duration of the stimulating signals to correspond to a time equivalent to from 10 to 25% of the T-Q diastole duration.

2. Apparatus in accordance with claim 1, wherein said means for initiating pressure pulsations is adapted to trigger stimulating signals within a window extending from 5% of the R-R path length before the expected end of the T-wave to 5% of the R-R path length after the end of the T-wave.

3. Apparatus in accordance with claim 1, wherein said means for measuring the heart rhythm comprises an electrocardioscope and an associated set of electrodes.

4. Apparatus in accordance with claim 1, wherein said means for measuring the heart rhythm comprises at least one of a pulse sensor and an electrocardiograph.

5. Apparatus in accordance with claim 4, wherein said pulse sensor is located at any point of a patient's body for generating pulse signals in response to the patient's heart rhythm and adapted to transmit signals by wireless transmission.

6. Apparatus in accordance with claim 4, wherein said pulse sensor comprises a belt worn around a patient's chest and wherein at least one transmitter is provided for transmitting signals derived from said pulse sensor to said means for producing pressure pulsations.

7. Apparatus in accordance with claim 1, wherein said means for producing pressure pulsations in the peripheral vascular system comprises a pulse generator for generating electrical signals and means for applying said electrical signals as stimulating signals to one or more skeletal or smooth muscles associated with said peripheral vascular system, whereby to produce said pressure pulsations in said peripheral vascular system.

8. Apparatus in accordance with claim 7, wherein said applying means comprises at least one neutral electrode and at least first and second active electrodes and wherein said electrical pulses are applied in a sequence to said first and second active electrodes, said at least one neutral electrode being connected to a neutral terminal of said pulse generator.

9. Apparatus in accordance with claim 8, wherein said sequence comprises a regularly repeating sequence.

10. Apparatus in accordance with claim 8, wherein said sequence comprises a random sequence.

11. Apparatus in accordance with claim 1 and further comprising a blood pressure measuring instrument for measuring a blood pressure of said mammal or other living organism.

12. Apparatus in accordance with claim 1, wherein said means for producing pressure pulsations in the peripheral vascular system comprises a pulse generator for generating electrical pulses and a pressure pulsation generator connected to receive said electrical pulses and generate pressure pulsations in response thereto and means for applying said pressure pulsations to a pressure pad adapted for mounting on a patient's body.

13. Apparatus in accordance with claim 12, wherein said pulse generator is adapted to produce trains of pulses, said pulses having a pulse repetition frequency, an amplitude, a pulse form, a pulse width and a pulse mode, and said trains having a duration and an pulse delay relative to a reference point of an ECG trace, and wherein means are provided for varying at least one of said pulse delay, said train duration, said pulse repetition frequency and said pulse amplitude.

14. Apparatus in accordance with claim 13, wherein said means for varying said pulse repetition frequency and said amplitude comprise manually adjustable means.

15. Apparatus in accordance with claim 13, wherein means are also provided for varying at least one said pulse form, said pulse width and said pulse mode.

16. Apparatus in accordance with claim 15, wherein said means for varying said pulse form, said pulse mode and said pulse width comprise manually adjustable means.

17. Apparatus in accordance with claim 13, wherein said pulse generator comprises a control unit and a memory for storing control settings of said control unit for the control of said pulse generator and wherein input means is provided permitting the inputting of control settings relating to at least said pulse delay, said train duration, said pulse frequency and said pulse amplitude.

18. Apparatus in accordance with claim 17, wherein means is also provided for varying at least one of a form of each pulse, a width of each of said electrical pulses and a mode of said electrical pulses and wherein said input means is also provided for inputting further control settings relating to said pulse form, said pulse mode and said pulse width.

19. Apparatus in accordance with claim 17, wherein said control unit and said memory are adapted to permit storage of data relating to at least one of a patient's pulse rate, blood pressure and the stimulation applied over a period of time.

20. Apparatus in accordance with claim 19, wherein said apparatus includes output means permitting output of said stored data.

21. Apparatus in accordance with claim 12, wherein said apparatus comprises a display means for displaying at least one of a patient's pulse rate, an ECG trace for said patient, a blood pressure trace for said patient, actual settings of said pulse generator and electrical settings for stimulating pulses applied to said patient.

22. Apparatus in accordance with claim 12, wherein said pulse generator comprises means for deriving from said heart rhythm for each period of said heart rhythm a time corresponding to an end of each T-wave of said heart rhythm and means for synchronizing the generation of pulses to coincide with the end of each said T-wave.

23. Apparatus in accordance with claim 1 and further comprising a safety means, said safety means being adapted to receive respective signals corresponding to an actual pulse rate and to one or more actual blood pressure values and to compare said actual pulse rate or said one or more blood pressure values with a respective preset value or values prevailing at the start of said treatment and to issue a warning signal or shut off said apparatus when at least one of said actual pulse rate and one or more actual blood pressure values exceeds a respective predetermined limit or a prevailing value at the start of said treatment.

24. Apparatus for treating a mammal or other living organism having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said organism having a pulse rate and a systolic pressure resulting from the action of the heart, the apparatus comprising means for measuring the heart rhythm, means for producing pressure pulsations in the peripheral vascular system by a non-invasive or invasive method in synchronization with the heart rhythm in the counterpulsation mode, means determining, for each periodically repeating heart rhythm, a time corresponding to an end of each T-wave, means for varying at least one parameter of such pressure pulsations to produce an optimized reduction in at least one of said pulse rate and said systolic pressure and thereby a net reduction in said heart load, means for initiating the pressure pulsations in the peripheral vascular system or at a muscle close to the heart by stimulation signals triggered in a time window lying within a range of 5% of the R-R path length before the end of the T-wave and 45% of the R-R path length after the end of the T-wave, means for selecting the duration of the stimulating signals to correspond to a time equivalent to from 10 to 25% of the T-Q diastole duration, said apparatus being in combination with a cardiostimulator, wherein said cardiostimulator defines said means for measuring the heart rhythm.

25. Apparatus in accordance with claim 24, wherein said means for producing pressure pulsations in the peripheral vascular system comprises a pulse generator integrated into said cardiostimulator.

26. Apparatus in accordance with claim 24, wherein said cardiostimulator is adapted to transmit a wireless signal corresponding to said heart rhythm and wherein said means for producing pressure pulsations in the peripheral vascular system is a muscle stimulator separate from said cardiostimulator and provided with a wireless receiver for receiving wireless signals transmitted by said cardiostimulator.

27. Apparatus in accordance with claim 24, wherein said cardiostimulator comprises a pacemaker, or a defibrillator, or a cardiomyo-stimulator.

28. Apparatus in accordance with claim 24 incorporated into at least one article of clothing.

29. Apparatus in accordance with claim 24 incorporated into a seat, said seat comprising one of a seat of a means of transport, an office chair, a chair for home use, a chair for clinic use and a chair for recreational purposes.

30. Apparatus in accordance with claim 24, wherein said means for measuring the heart rhythm produces a heart rhythm signal, wherein means is provided for producing a systolic blood pressure signal, and wherein said means for producing pressure pulsations comprises a pulse generator having a controller, said controller being adapted to receive said heart rhythm signal and said systolic pressure signal and to control the pulse generator using a signal formed by a combination of said heart rhythm signal and said systolic blood pressure signal.

31. Apparatus in accordance with claim 30, wherein means is provided for comparing said heart rhythm signal with a reference to form a heart rhythm factor, wherein means is provided for comparing said systolic blood pressure signal with a reference to form a systolic blood pressure factor, wherein means is provided for multiplying said heart rhythm factor and said systolic blood pressure factor to produce a resulting factor, and wherein said controller for said pulse generator is adapted to control said pulse generator to minimize said resulting factor.

32. Apparatus in accordance with claim 24 further comprising a safety means, said safety means comprising means for monitoring at least one parameter of the means used for producing pressure pulsations in the peripheral vascular system and for comparing said parameter with at least one predetermined value limit and means for discontinuing the treatment or triggering an alarm should the monitored parameter exceed or fall short of said predetermined value limit.

33. Apparatus in accordance with claim 32, wherein said predetermined value limit comprises at least one of a maximum or minimum value of a said parameter, a minimum or maximum gradient of a rate of change of the said parameter over time, a statistical deviation over time of a said parameter, or any combination of the foregoing.

34. Apparatus in accordance with claim 24 comprising gating means for defining a window between successive R-R peaks within which sensed signals are inhibited from triggering stimulation signals, and wherein said gating means is preferably adjustable to vary the width and/or position of the window relative to the R-R cycle.

35. Apparatus in accordance with claim 34 including timing means for triggering a stimulation signal after a delay following each R-peak corresponding to a minimum delay plus an offset delay, adaptive means for varying said offset delay in steps while monitoring one of the heart beat rhythm and the product of the heart beat rhythm and the systolic blood pressure and for identifying the offset delay which results in the lowest heart beat or lowest heart load and for subsequently operating the apparatus with this offset delay for the patient involved.

36. A method of treating a mammal or other living organism having a heart, a heart rhythm comprising periodically repeating Q, R, S and T waves of an electrocardiogram and a peripheral vascular system to achieve a heart load reduction, said electrocardiogram exhibiting a repeating QRSTQ heart rhythm having a Q-T systole duration, a T-Q diastole duration and an R-R path length, said organism having a pulse rate and a systolic pressure resulting from the action of the heart, the method comprising the steps of:

measuring the heart rhythm, producing pressure pulsations in the peripheral vascular system by a non-invasive or invasive method in synchronization with the heart rhythm in a counterpulsation mode, determining, for each periodically repeating heart rhythm, a time corresponding to an end of each T-wave, varying at least one parameter of an input system generating said pressure pulsations to produce an optimized reduction in at least one of said pulse rate and said systolic pressure and thereby a net reduction in said heart load, initiating the pressure pulsations in the peripheral vascular system by stimulation signals triggered in a time window lying within a range of 5% of an R-R path length before an end of a T-wave and 45% of the R-R path length after the end of the T-wave, and selecting a duration of the stimulating signals to correspond to a time equivalent to from 10 to 25% of the T-Q diastole duration.

37. A method in accordance with claim 36, comprising the further step of adjusting the time at which stimulation is applied to said living organism by said input system to compensate for the reduction in pulse rate resulting from the treatment.

38. The method of claim 36, wherein pressure pulsations are produced by subjecting the mammal to stimulating impulses of electrical energy at a position of the peripheral vascular system at which a smooth muscle or a skeletal muscle is present, excluding the heart and wherein the parameter varied is selected from the group comprising:

- the impulse delay before the start of counterpulsation, said impulse delay being the time difference between the Q-wave end of a QRS heart rhythm signal and the start of a train of stimulating impulses generating pressure pulsation,
- the train duration, i.e. the time between the start and end of a train of stimulating impulses within one QRS heart rhythm,
- the impulse width, i.e. the time between the start and end of each stimulating impulse of each said train,
- the frequency of the impulses forming a train of stimulating impulses generating pressure pulsation,
- the amplitude of stimulating impulses generating pressure pulsation,
- the impulse form, being the geometric form of the stimulating impulse resulting when an amplitude of the impulse is displayed over a full impulse duration,
- the impulse mode, being the relationship between positive and negative half cycles of each said electrical stimulating impulse.

39. A method in accordance with claim 36 used to treat a human being to achieve benefits in one or more fields selected from the following group:

- promotion of fitness and wellness,
- physical training for sport,
- aesthetic medicine, including any kind of desired body shaping and/or tissue changes, e.g. due to body fat burning (lipolysis), fluid drainage and tissue and muscle growth and/or reduction as well as associated skin changes,
- curative medicine, including invasive and non-invasive methods, and
- cosmic medicine.

40. A method in accordance with claim 36, wherein said method is carried out in the field of curative medicine, or for the prevention of disease and/or rehabilitation in at least one of the following fields:

- for anesthesiology, to reduce the risk of acute heart failure,
- for cardiology, to remedy tachycardia, ischemic heart disease, cardiomyopathy, hypertension, heart failure, valvular pathology,
- for angiology, for lymph-venous and arterial insufficiencies,
- for orthopaedy and neurology, to remedy hypotrophy and atrophy of muscles,
- for pain reduction, including anti-pain TENS-treatment for any kind of pathology in the body support and motion system of a human being, including osteochondrosis,
- for urology and proctology, for sphincter insufficiencies,
- for gynecology and sexology, for the treatment of dilatatio vaginae, descendus uteri, adnexitis, amenorea, frigidity,
- for endocrinology, for adipositas partialis, hypomastia,
- for surgery, for diastasis musculi recti abdominis, decubiras, and
- for cosmic medicine, to preserve muscle tone of astronauts.

* * * * *